(12) United States Patent
Faulhaber

(10) Patent No.: US 12,083,024 B2
(45) Date of Patent: Sep. 10, 2024

(54) VERTEBRAL IMPLANTS AND RELATED METHODS OF USE

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 74 days.

(21) Appl. No.: 17/931,282

(22) Filed: Sep. 12, 2022

(65) Prior Publication Data

US 2023/0000642 A1  Jan. 5, 2023

Related U.S. Application Data

(63) Continuation of application No. 17/153,127, filed on Jan. 20, 2021, now Pat. No. 11,446,158, which is a continuation of application No. 16/293,778, filed on Mar. 6, 2019, now Pat. No. 10,918,496, which is a continuation of application No. 15/874,253, filed on Jan. 18, 2018, now Pat. No. 10,265,190, which is a continuation of application No. 14/466,632, filed on Aug. 22, 2014, now Pat. No. 9,907,669.

(51) Int. Cl.
  *A61F 2/44* (2006.01)
  *A61F 2/46* (2006.01)
  *A61F 2/30* (2006.01)

(52) U.S. Cl.
  CPC .............. *A61F 2/4455* (2013.01); *A61F 2/44* (2013.01); *A61F 2/4465* (2013.01); *A61F 2/447* (2013.01); *A61F 2/4611* (2013.01); *A61F 2002/30387* (2013.01); *A61F 2002/30507* (2013.01); *A61F 2002/3052* (2013.01); *A61F 2002/30556* (2013.01); *A61F 2002/30578* (2013.01); *A61F 2002/30579* (2013.01); *A61F 2002/30593* (2013.01); *A61F 2002/30604* (2013.01); *A61F 2002/30878* (2013.01); *A61F 2002/4415* (2013.01); *A61F 2002/4485* (2013.01); *A61F 2002/4627* (2013.01)

(58) Field of Classification Search
  CPC ............ A61F 2002/30578; A61F 2002/30604; A61F 2/44; A61F 2002/443; A61F 2/441; A61F 2/4455; A61F 2/447; A61B 17/7044; A61B 17/7059
  See application file for complete search history.

(56) References Cited

U.S. PATENT DOCUMENTS 8,137,401 B2 * 3/2012 Stad ..................... A61F 2/442
                                                      623/17.11

FOREIGN PATENT DOCUMENTS

WO   WO-2013184946 A1 * 12/2013 ........... A61F 2/4465

* cited by examiner

*Primary Examiner* — Larry E Waggle, Jr.

(57) ABSTRACT

A vertebral insert may include a first linkage, a second linkage, and a third linkage. The first, second, and third linkages may at least partially defining a cavity. The insert may be movable between a collapsed configuration and an expanded configuration, and the movement of the first and second linkages with respect to one another may be configured to reciprocally move the insert between the collapsed and expanded configurations.

18 Claims, 16 Drawing Sheets

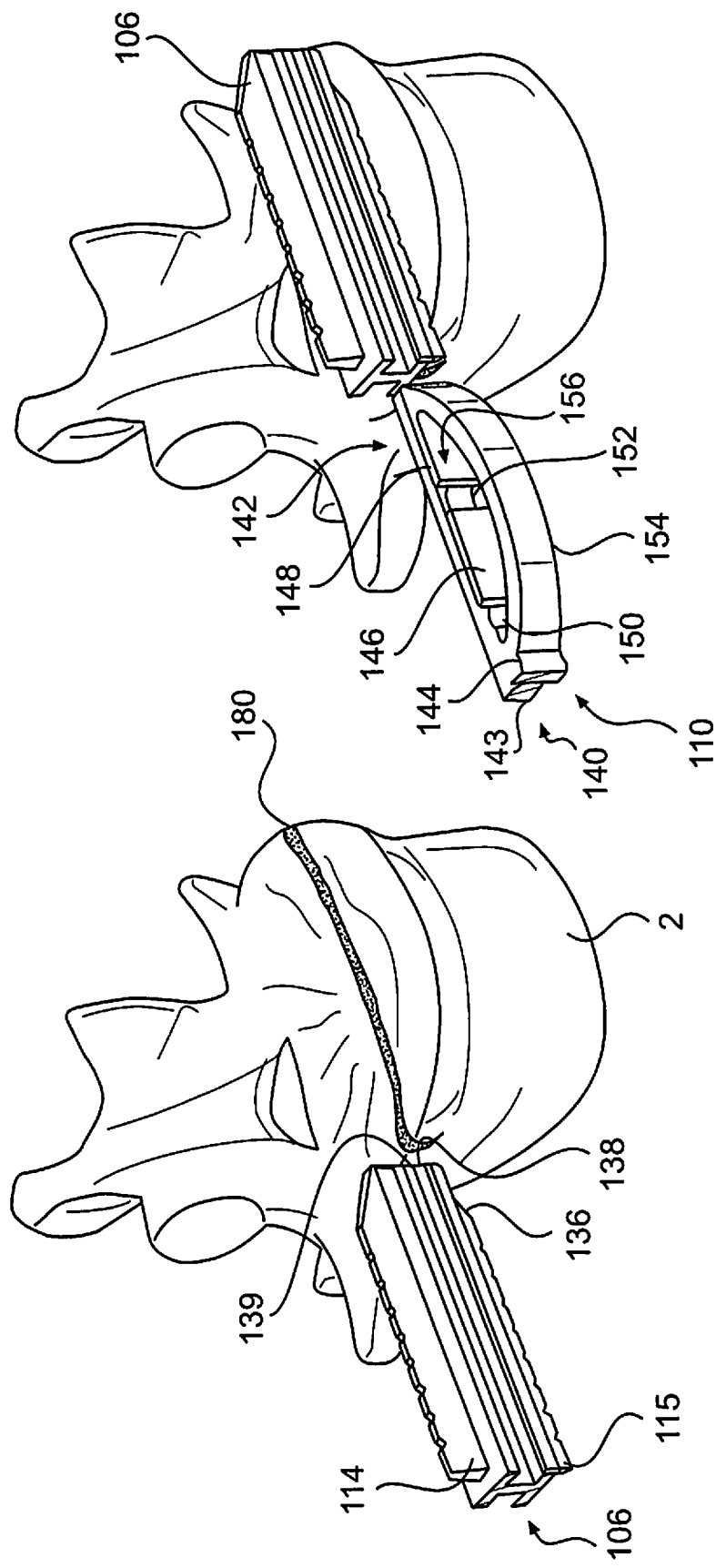

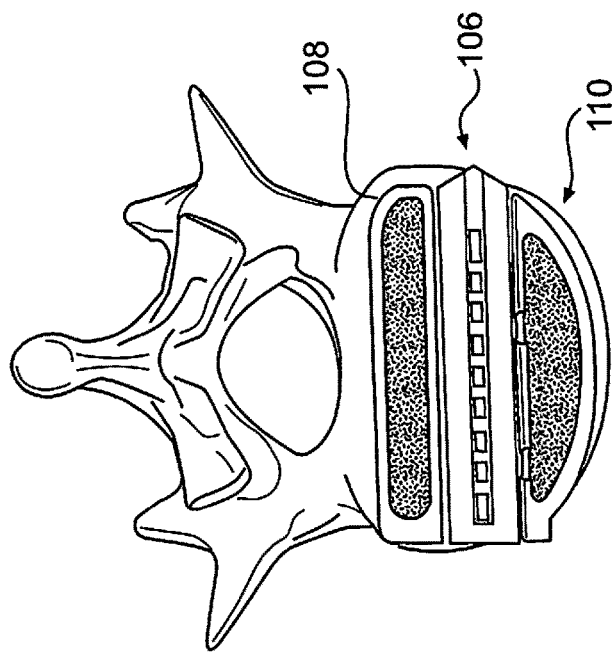
FIG. 8
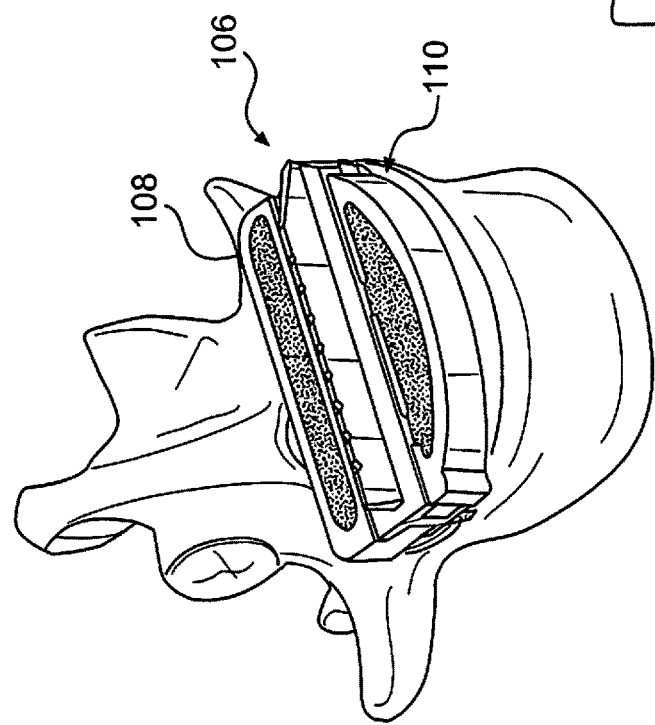
FIG. 9
FIG. 7

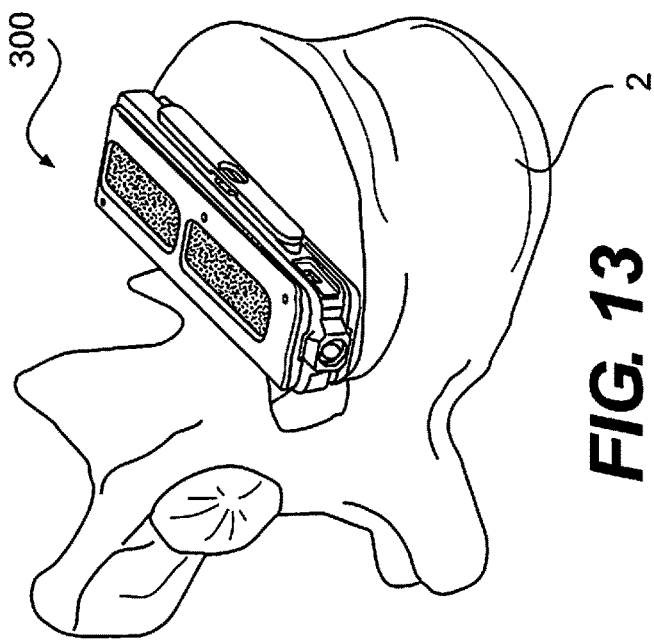
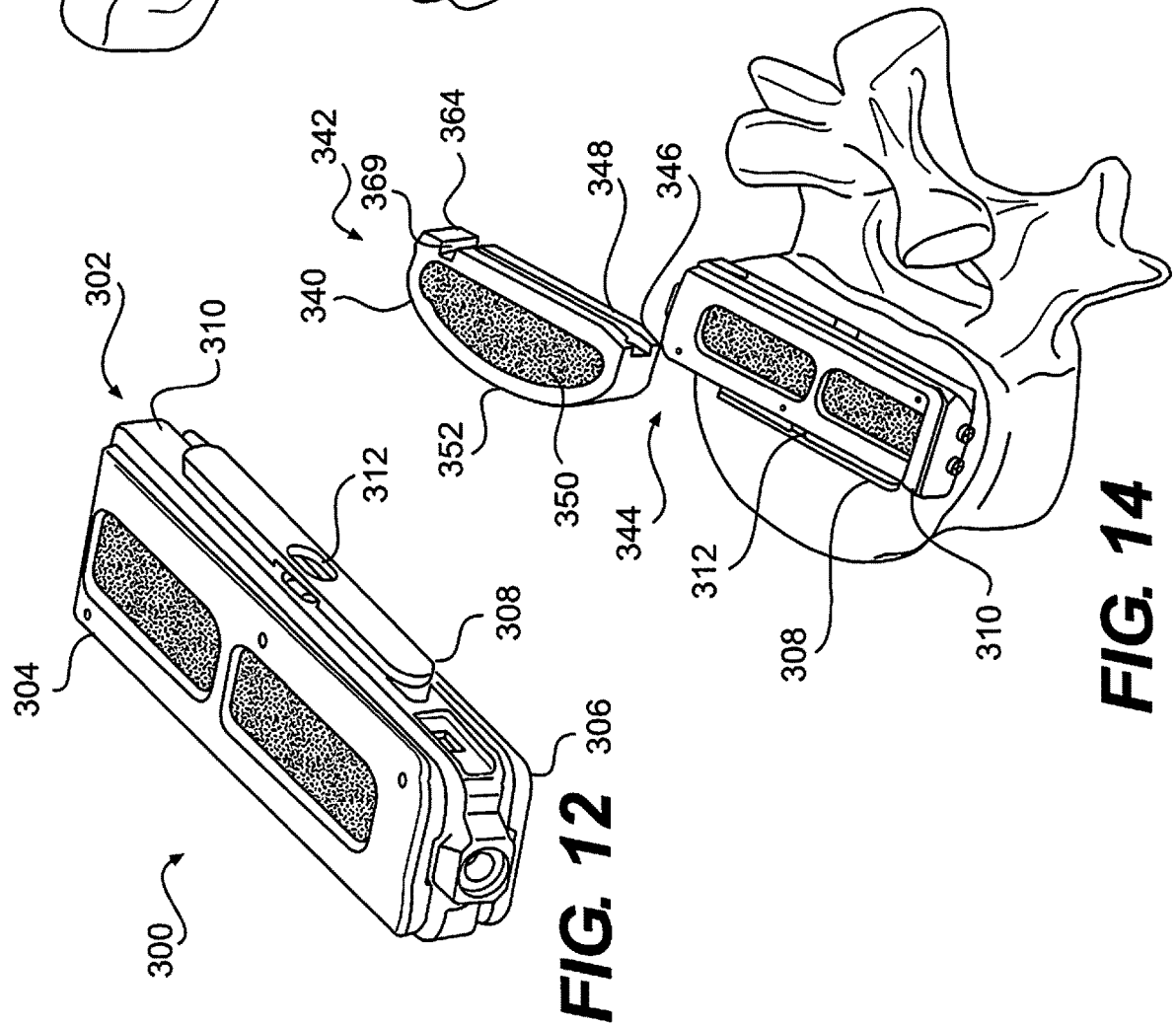

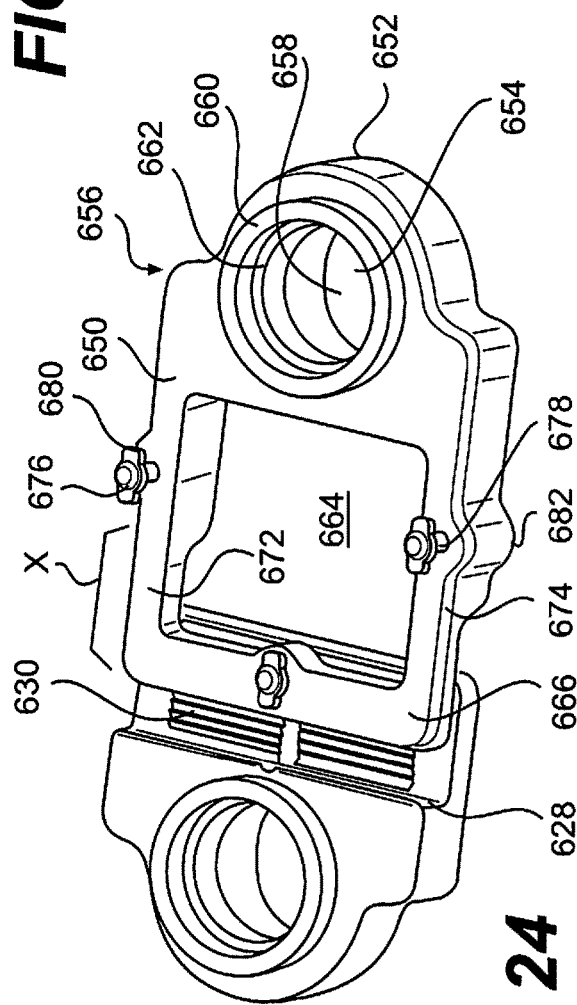
FIG. 23
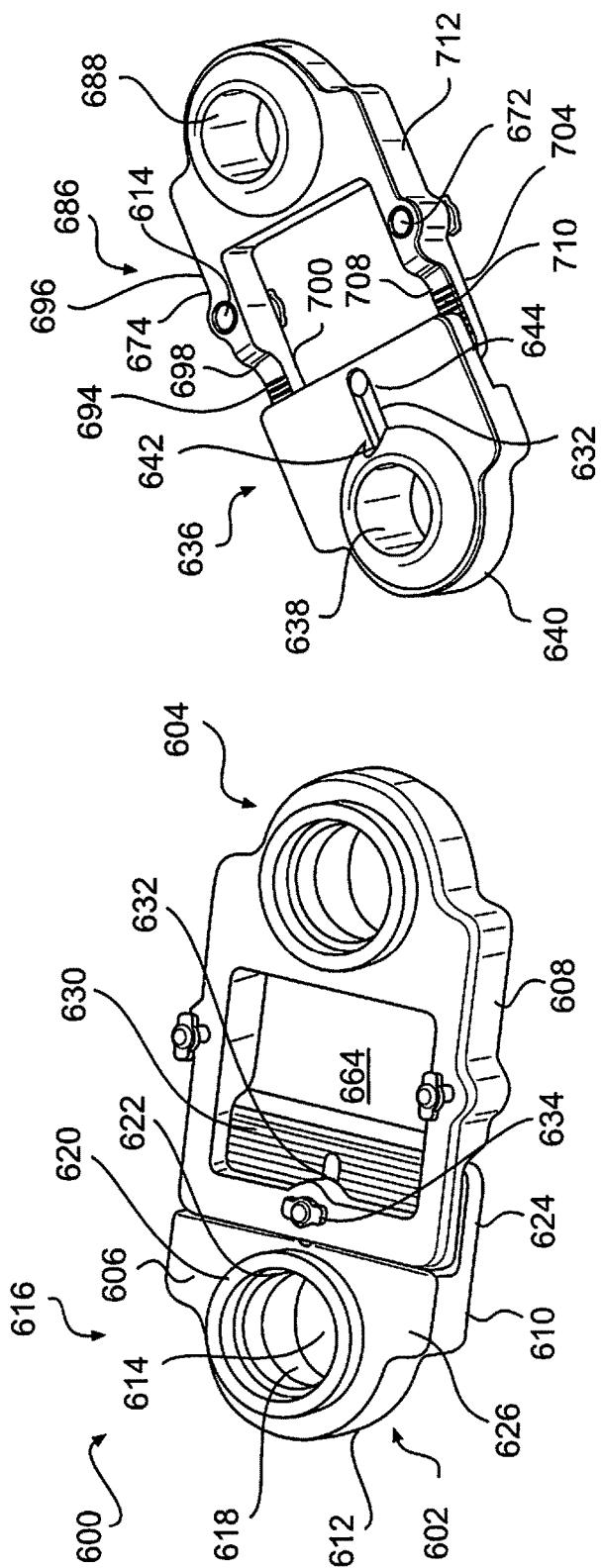
FIG. 22
FIG. 24

VERTEBRAL IMPLANTS AND RELATED METHODS OF USE

CROSS-REFERENCE TO RELATED APPLICATION

The present application a continuation of U.S. patent application Ser. No. 17/153,127, filed Jan. 20, 2021, which is a continuation of U.S. patent application Ser. No. 16/293,778 filed Mar. 6, 2019, published as U.S. Pat. Pub. No. 2019-0192311, which is a continuation of U.S. patent application Ser. No. 15/874,253 filed Jan. 18, 2018, now U.S. Pat. No. 10,265,190, which is a continuation of U.S. patent application Ser. No. 14/466,632, filed Aug. 22, 2014, now U.S. Pat. No. 9,907,669, the entire disclosures of all of which are incorporated herein by reference in their entireties for all purposes.

FIELD OF THE INVENTION

Various examples of the present disclosure relate generally to vertebral inserts, such as, e.g., fusion devices and related systems and methods. More specifically, the present disclosure relates to vertebral inserts, devices, systems, and methods for repairing and/or replacing intervertebral discs of a patient.

BACKGROUND

A common procedure for handling pain associated with intervertebral discs that have become degenerated due to various factors such as trauma or aging is the use of intervertebral spacers to fuse, e.g., one or more adjacent vertebral bodies. Generally, to fuse the adjacent vertebral bodies, the native intervertebral disc is first partially or fully removed. An intervertebral spacer is then typically inserted between neighboring vertebrae to maintain normal disc spacing and restore spinal stability, thereby facilitating an intervertebral fusion.

There are a number of known conventional intervertebral spacers and methodologies in the art for accomplishing the vertebral fusion. These include screw and rod arrangements, solid bone implants, and intervertebral spacers which include a cage or other implant mechanism which, typically, may be packed with bone and/or bone-growth inducing substances. These devices are implanted between adjacent vertebral bodies in order to fuse the vertebral bodies together, potentially alleviating any associated pain.

However, there are drawbacks associated with the known conventional intervertebral spacers and methodologies. For example, some conventional intervertebral spacers may lack sufficient surface area to optimally fuse adjacent vertebral bodies.

SUMMARY OF THE DISCLOSURE

The present disclosure relates to examples of interbody vertebral inserts and related methods of use.

In one aspect, the present disclosure is directed to a vertebral insert. The vertebral insert may include a first linkage, a second linkage, and a third linkage. The first, second, and third linkages may at least partially defining a cavity. The insert may be movable between a collapsed configuration and an expanded configuration, and the movement of the first and second linkages with respect to one another may be configured to reciprocally move the insert between the collapsed and expanded configurations.

In another aspect, the present disclosure is directed to a method of installing an expandable vertebral insert. The method may include inserting the vertebral insert between two vertebral bodies while the vertebral insert is in a collapsed configuration. The vertebral insert may include a first linkage, a second linkage, and a third linkage. The first, second, and third linkages may at least partially define a cavity. The insert may be movable between a collapsed configuration and an expanded configuration. The movement of the first and second linkages with respect to one another may be configured to reciprocally move the insert between the collapsed and expanded configurations. The method also may include expanding the vertebral insert to an expanded configuration such that a cavity defined by the vertebral insert is larger in the expanded configuration than in the collapsed configuration.

In yet another aspect, the present disclosure is directed to a vertebral insert. The vertebral insert may include a support member having a superior surface, an inferior surface, a first groove disposed between the superior surface and inferior surface on a first lateral side, a second groove disposed between the superior surface and inferior surface on a second lateral side, and a first keel extending from one of the superior and inferior surfaces. The vertebral insert also may include a first lateral spacer having a portion configured to extend within the first groove, and a second lateral spacer having a portion configured to extend within the second groove.

In yet another aspect, the present disclosure is directed to a vertebral spacer system. The system may include a vertebral spacer, and a bracket coupled to the vertebral spacer. The system also may include a first plate, and a second plate coupled to the first plate and the bracket. The second plate may be movable relative to the first plate, and the second plate may define a cavity through which the vertebral spacer extends.

In yet another aspect, the present disclosure is directed to a method of treating a patient. The method may include attaching a first plate to a first vertebral body, and attaching a second plate to a second vertebral body. The first plate and the second plate may be coupled to one another. The method also may include moving the first and second plates away from one another to distract the first and second vertebral bodies, and inserting a vertebral insert through a cavity defined by the second plate.

In yet another aspect, the present disclosure is directed to a method of treating a patient. The method may include inserting a vertebral insert into the intervertebral space between two adjacent vertebral bodies, and expanding the vertebral insert to distract the adjacent vertebral bodies. The method also may include inserting a spacer into the intervertebral space, and laterally coupling the spacer to the vertebral insert after expanding the vertebral insert.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

FIGS. 3-9 depict an exemplary method of installing a vertebral insert in accordance with an example of the present disclosure.

FIG. 12 is perspective view of a vertebral insert in accordance with an example of the present disclosure.

FIGS. 13-16 depict an exemplary method of installing a vertebral insert in accordance with an example of the present disclosure.

FIGS. 22-24 are perspective views of a plate assembly in accordance with an example of the present disclosure.

DETAILED DESCRIPTION

Reference will now be made in detail to examples of the present disclosure, examples of which are illustrated in the accompanying drawings. Wherever possible, the same reference numbers will be used throughout the drawings to refer to the same or like parts.

Figure 1:
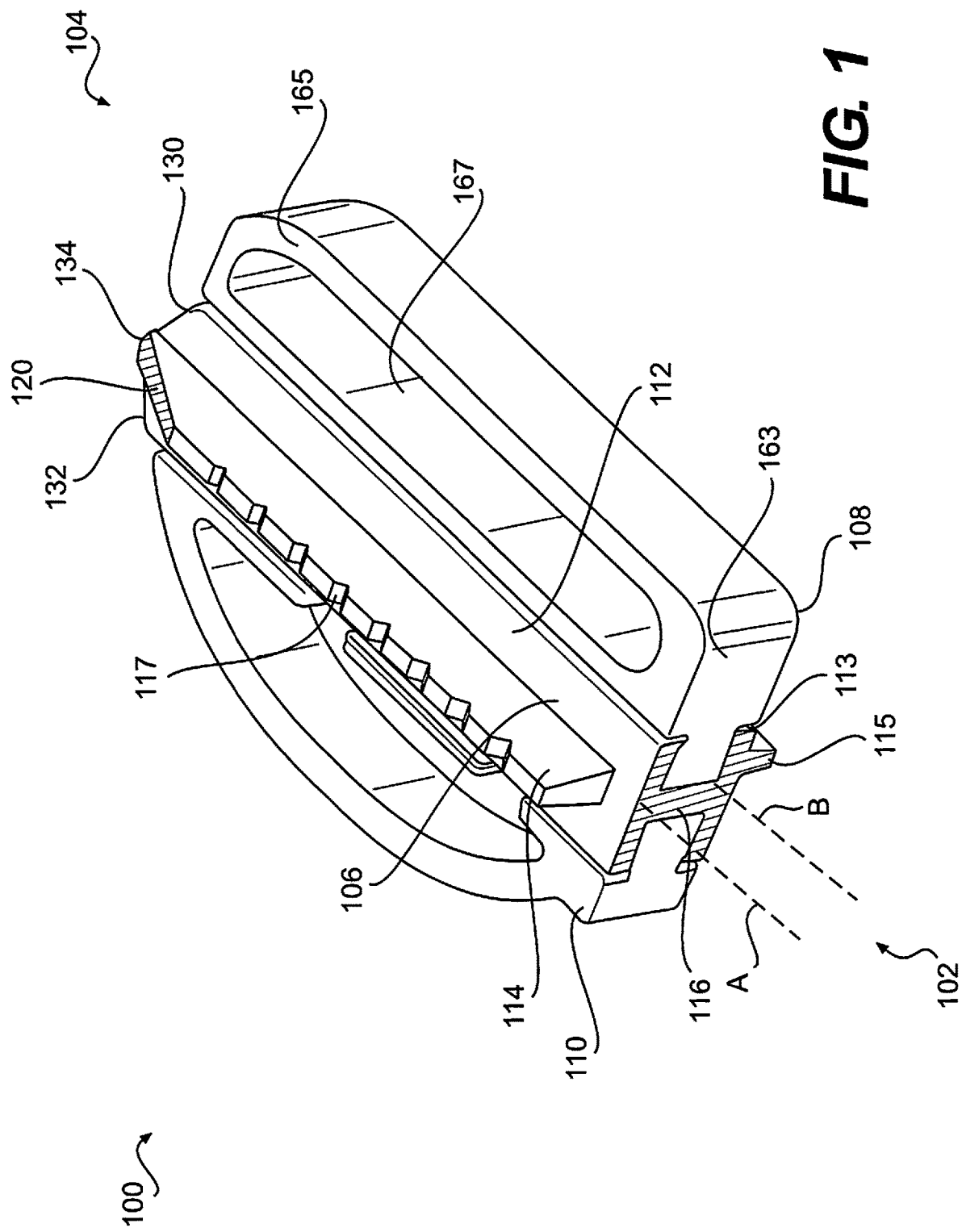
FIG. 1 is a perspective view of a vertebral insert in accordance with an example of the present disclosure.

A vertebral insert 100 shown in FIG. 1 may extend from a first end 102 toward a second end 104, and include a support member 106, a first lateral insert 108 and a second lateral insert 110. Support member 106, and first and second lateral inserts 108, 110 may be formed from a rigid, biocompatible material such as, e.g., titanium or polyetheretherketone (PEEK), among others. Support member 106 and first and second lateral inserts 108, 110 may be formed of the same or different materials. In one example, support member 106 may be formed from titanium while first and second lateral inserts 108, 110 are formed from PEEK. Components that contact bone, including support member 106, and first and second lateral inserts 108, 110, may be treated with a titanium and/or hydroxyapatite plasma spray coating to encourage bony on-growth, improving the strength and stability of the connection between the respective component and the underlying bone (e.g., a vertebral body). Any other suitable coating also may be provided on one or more surfaces of support member 106, and first and second lateral inserts 108, 110. Such coatings may include therapeutic and/or antibiotic agents, if desired. Support member 106 and first and second lateral inserts 108, 110 also may include radiopaque markings to facilitate in vivo visualization and insertion.

Figure 2:
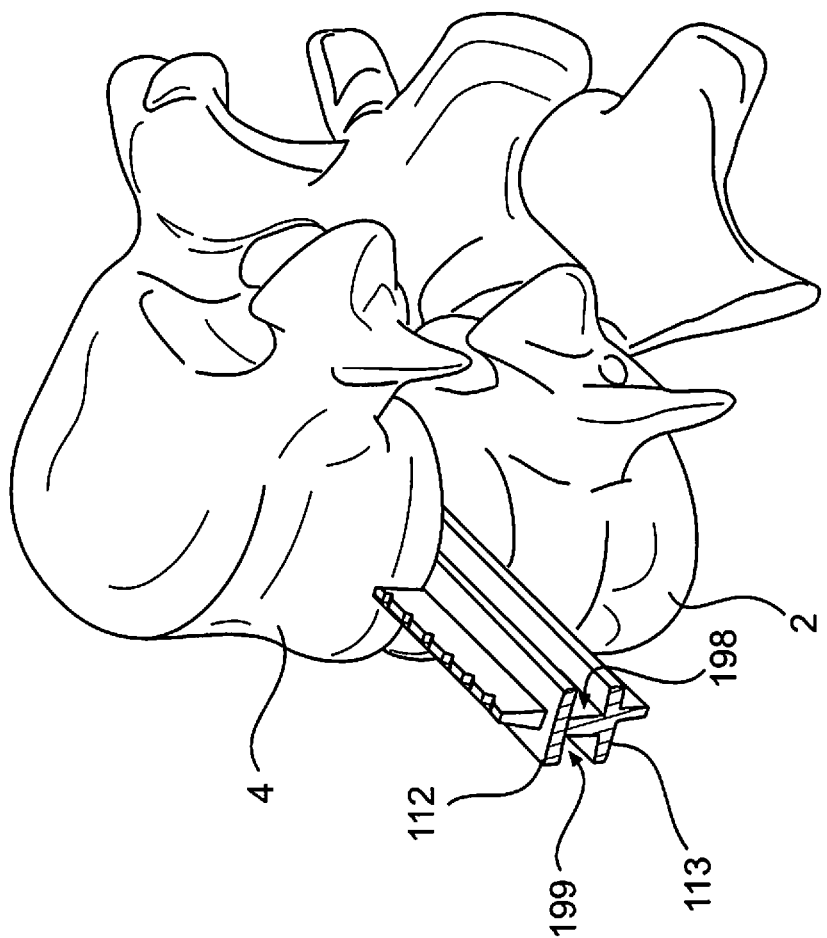
FIG. 2 is a perspective view of a support member disposed between adjacent vertebral bodies in accordance with an example of the present disclosure.
Figure 6:
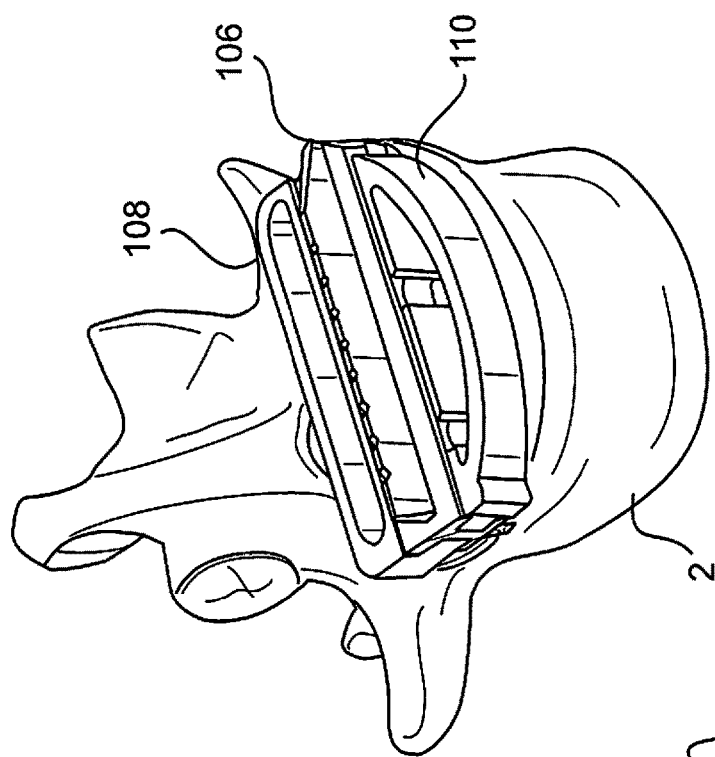
Figure 5:
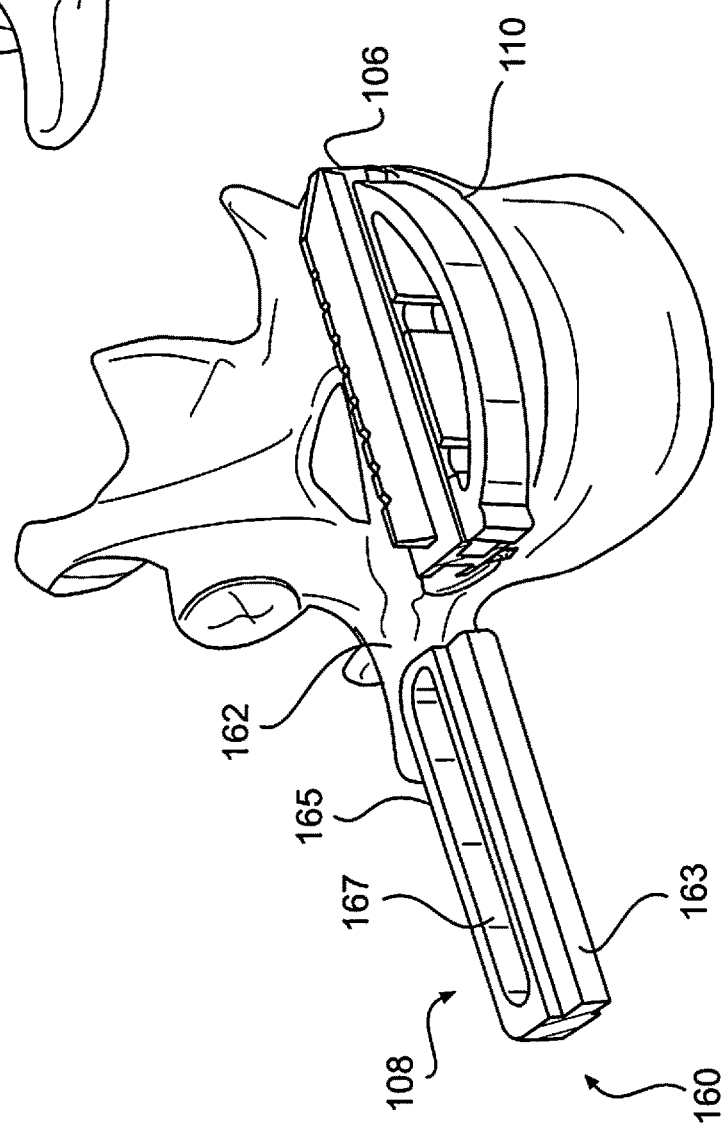

Support member 106 may have an upper or superior surface 112 and a lower or inferior surface 113. In some examples, superior surface 112 and inferior surface 113 may be substantially parallel to one another, or may have another suitable relationship to one another. In one example, superior surface 112 and/or inferior surface 113 may have a substantially flat configuration. In some examples, superior surface 112 and/or inferior surface 113 may have a variable cross-section, such as, e.g., bi-convex, e.g., curved from left to right and front to back, or may have another suitable configuration. This curvature may give superior surface 112 and/or inferior surface 113 a partial dome or spherical shape. The curvature may be complementary to the natural curvature of an adjacent vertebral body and may provide for an anatomical fit between superior surface 112 and/or inferior surface 113 with a vertebral body (shown in FIG. 2). Superior surface 112 and inferior surface 113 may be substantially similar to one another or may have different features. In one example, superior surface 112 and inferior surface 113 may be mirror images of one another. Superior surface 112 may be coupled to inferior surface 113 by a member 116. Superior surface 112, inferior surface 113, and member 116 may generally form an I-beam type configuration defining a first groove 198 and a second groove 199 (referring to FIG. 2). That is, a groove 198 may be disposed between superior and inferior surfaces 112 and 113 at a first lateral side of vertebral insert 100, and a groove 199 may be formed between superior and inferior surfaces 112 and 113 at a second lateral side of vertebral insert 100.

One or more keels 114 may be located on superior surface 112 and may extend away from superior surface 112 at an angle. In one embodiment, the one or more keels 114 may include a plurality of serrations or other geometric configurations. In the example shown in FIG. 1, keel 114 may be formed at least partially from a substantially elongate member having one or more notches 117 disposed on an axial end surface of keel 114. However, in some examples, a plurality of keels that are longitudinally or laterally spaced from one another may extend away from superior surface 112. Once a discectomy has been completed, removing the damaged natural disc or damaged disc material, a groove or channel 180 (shown in FIG. 3) may be cut into the vertebral body to receive keel 114. Keel 114 may be integrally formed with superior surface 112 or may alternatively be attached to superior surface 112 by a suitable securing mechanism, e.g., an adhesive. Keel 114 may have one more holes, e.g., through holes, or openings (not shown) perpendicular to the longitudinal axis of the keel. These holes or openings may provide an aperture for bony in-growth, which may strengthen the connection or interface between the endplate and the vertebral body. In some examples, a plurality of keels 114 may be arranged in a plurality of rows and/or columns, if desired, which can be inserted through a similarly arranged sequence of channels or grooves formed in a vertebral body. Keels 114 may include suitable coatings or other geometrical features (e.g., barbs or other protrusions) to promote bony in-growth/on-growth. In examples having a plurality of keels 114, each keel 114 may have varying lengths, widths, and/or other dimensions. One or more keels 115 (which may include one or more of the aforementioned features of keels 114) may be located on inferior surface 113 and may extend away from inferior surface 113 at an angle.

Keel 114 may include a ramp 120 at the second, leading end 104 of vertebral insert 100. Superior surface 112 may include two inclined edges directed laterally inward toward a first longitudinal axis A at second, leading end 104. Longitudinal axis A may extend longitudinally through the longitudinal midsection of superior surface 112. A first inclined edge 130 of superior surface 112 may incline from a first lateral side of vertebral insert 100 toward longitudinal axis A, while a second inclined edge 132 of superior surface 112 may incline from a second lateral side of vertebral insert 100 toward longitudinal axis A. Ramp 120 and inclined edges 130 and 132 may generally converge at a point 134 disposed along longitudinal axis A. Keel 115 may include a ramp 136 (shown only in FIG. 3) that may include one or more features of ramp 120 of keel 114. Inferior surface 113 may include a first inclined edge (not shown) and a second inclined edge 138 that may include one or more of the features of first and second inclined edges 130 and 132 of superior surface 112. The first inclined edge and second inclined edge 138 of keel 115 may converge toward a second longitudinal axis B. Longitudinal axis B may extend longitudinally through the longitudinal midsection of inferior surface 113. The first inclined edge and second inclined edge 138 of inferior surface 113 and ramp 136 of keel 115 may generally converge at a point 139 that is disposed along longitudinal axis B.

The bladed or wedged formation of second, leading end 104 of vertebral insert 100 may form the leading insertion end of vertebral insert 100 (e.g., the end that enters the intervertebral space first). The bladed or wedged formations may possess a mechanical advantage over other configurations. More specifically, the bladed or wedged formations may reduce the amount of force required to insert vertebral insert 100 into a patient. Further, in some examples, the portion of support member 106 at first end 102 may be the trailing end of support member 106 (e.g., the end that enters the patient second or last). The trailing end of support member 106 may be inserted between vertebral bodies by any suitable mechanism including, e.g., hammering, sliding, pushing, or other mechanisms.

First lateral spacer 108 may include an elongate member 163 that extends from a first, trailing end 160 toward a second, leading end 162. In some examples, elongate member 163 may be generally cuboid, although other suitable configurations, e.g., cylindrical or the like, are also contemplated. Elongate member 163 may cooperate with groove 198 or 199 to couple support member 106 with first lateral spacer 108. That is, elongate member 163 and groove 198 or 199 may form, e.g., a tongue and groove joint, although other suitable joints and mating relationships are also contemplated. A generally ellipsoid (or otherwise elongated) ring 165 may be partially defined by flange portions 170 and 172, and may extend from elongate member 163. The ellipsoid ring 165 may at least partially define the outer perimeter of a cavity 167. Cavity 167 may have a generally ellipsoidal (or otherwise elongated) cylindrical shape, although other suitable configurations are also contemplated. In some examples, the outer curvature of ellipsoid ring 165 may be determined by the posterior curvature of the vertebral bodies between which vertebral insert 100 is implanted.

Cavity 167 may be filled with bone graft or similar bone-growth inducing material to further promote and facilitate the intervertebral fusion. Cavity 167, in one example, may be packed with bone graft or similar bone-growth inducing material to promote the growth of bone through and around the vertebral insert. Such bone graft may be packed into cavity 167, subsequent to, or during implantation of the vertebral insert 100.

Second lateral spacer 110 may include an elongate member 143 that extends from a first, trailing end 140 toward a second, leading end 142 (referring to FIG. 4). In some examples, elongate member 143 may be generally cuboid, although other suitable configurations, e.g., cylindrical, are also contemplated. Elongate member 143 may cooperate with groove 198 or 199 to couple support member 106 with second lateral spacer 110. That is, elongate member 143 and groove 198 or 199 may form, e.g., a tongue and groove joint, although other suitable joints and mating relationships are also contemplated. Flange portions 144, 146, and 148 may extend away from a lateral end surface of elongate member 143 in the superior and inferior directions forming a generally t-shaped cross section with elongate member 143. In some examples, flange portions 144, 146, and 148 may mate and/or cooperate with lateral end surfaces of superior surface 112 and inferior surface 113, respectively. A groove 150 may be disposed longitudinally between flange portions 144 and 146, while a groove 152 may be disposed between flange portions 146 and 148. It should be noted that while two grooves and three flanges are shown in some examples, any other suitable number of grooves and flanges alternatively may be utilized to improve graft area, and/or ease of machining, among other factors. An arc portion 154 may extend laterally outward between first end 140 and second end 142. Arc portion 154, flanges 144, 146, and 148, and grooves 150 and 152 may define a cavity 156. In some examples, flanges 144, 146, 148, and arc portion 154 may define a generally D-shaped ring. It should be noted that, in some examples, the curvature of arc portion 154 may approximate the anterior curvature of adjacent vertebral bodies between which vertebral insert 100 is inserted. Cavity 156 may be filled with bone graft or other bone-growth inducing material in a substantially similar manner as described with respect to cavity 167.

In some examples, vertebral insert 100 may be delivered by a minimally invasive (MIS) lateral lumbar interbody fusion (LLIF) approach. Vertebral insert 100 may be configured to provide increased surface area over conventional vertebral inserts. Vertebral insert 100 may be self-distracting with the insertion of keels 114, 115, and may decrease the chance of subsidence. In some examples, vertebral insert 100 may not need additional fixation such as, e.g., plates or other locking systems because keels 114 and 115 may prevent vertebral insert 100 from backing out of the intervertebral space. That is, vertebral insert 100 may be a stand-alone implant. Vertebral insert 100 may provide improved spacer fit by allowing for anterior and posterior spacer selection. In some examples, vertebral insert 100 may provide increased total surface area contact with vertebral bodies while also engaging harder bone around the apophyseal ring. In still further examples, vertebral insert 100 may provide for increased amount of bone graft or bone-growth inducing substances to be utilized over conventional devices.

FIGS. 3-9 illustrate an exemplary installation sequence for vertebral insert 100. Initially, a groove 180 may be formed through the superior surface of a vertebral body 2. A groove 182 (shown only in FIG. 9) also may be formed in the inferior surface of vertebral body 4. Keels 115 and 114 of support 106 then may be aligned with grooves 180 and 182, respectively. Support 106 then may be inserted between vertebral bodies 2 and 4 by a suitable mechanism to place keels 115 and 114 into the grooves formed in the vertebral bodies, and to place superior and inferior surfaces 112 and 113 into the intervertebral space. Once support 106 is secured between vertebral bodies 2 and 4, one or more lateral inserts (e.g., first and second lateral inserts 108, 110) may be aligned with one or more grooves 198, 199 of support 106 and inserted between vertebral bodies 2 and 4. It should be noted that any suitable lateral insert may be selected to mate with support 106. Thus, the use of support 106 may permit operator flexibility and discretion when installing vertebral insert 100. For example, one or both of first and second lateral spacers 108, 110 may include modifications to, e.g., outer curvature, height, lordosis correction, or other features depending on the specific geometry of vertebral bodies 2 and 4. In some examples, lateral spacers 108 and 110 may provide for a continuous amount of lordotic correction, or alternatively, may each be configured to provide a different amount of lordotic correction to various portions of the vertebral bodies. In some examples, vertebral insert 100 may provide a higher amount of height and lordotic correction by having separate anterior and posterior spacers. In some examples, vertebral insert 100 may allow for evenly distributed weight loads. Lateral spacers 108 and 110 may be secured between vertebral bodies 2 and 4 by any suitable mechanism. In one example, rotatable locking flanges or screws (not shown) may be disposed at the trailing end of support 106. After lateral spacers 108 and 110 are inserted between the vertebral bodies 2 and 4, the locking flanges or screws may be rotated into a locking position to prevent spacers 108 and 110 from backing out of the intervertebral space.

Figure 10:
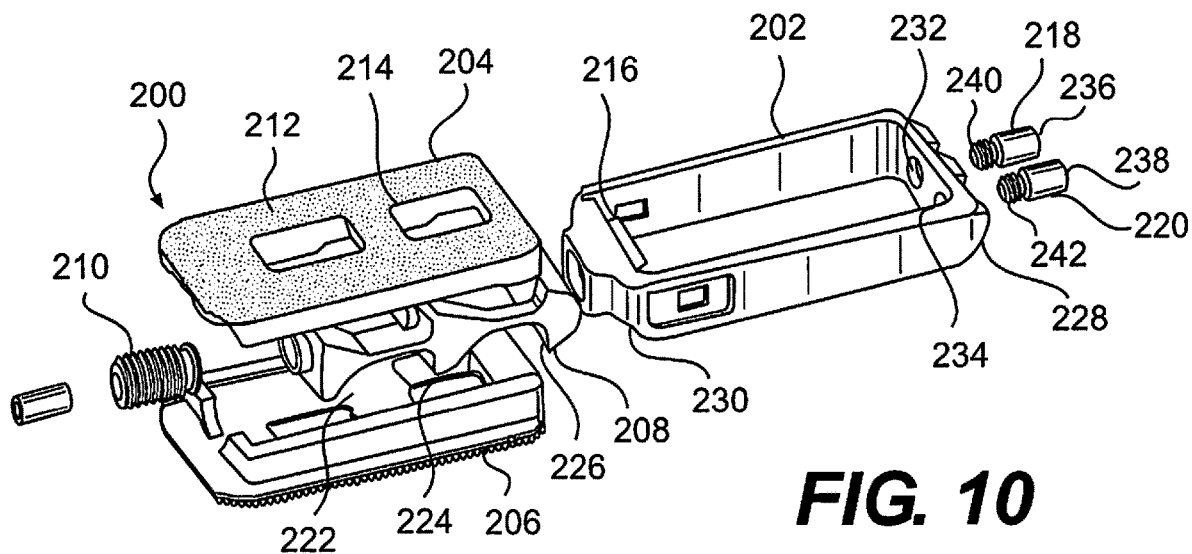
FIG. 10 is an exploded view of a vertebral insert in accordance with an example of the present disclosure.
Figure 11:
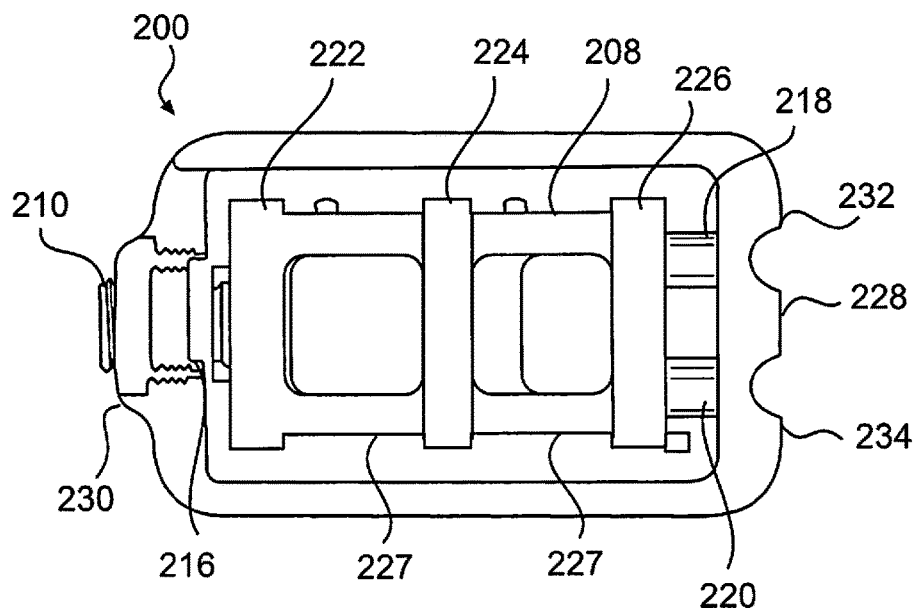
FIG. 11 is a top view of the vertebral insert of FIG. 10 with an endplate removed.

FIGS. 10 and 11 show different views of a vertebral insert 200, in accordance with a further aspect of the present disclosure. The vertebral insert 200 may include a body portion 202, a first endplate 204, a second endplate 206, a translation member 208, and an actuation member 210. Translation member 208 and actuation member 210 may cooperate to axially (e.g., vertically) move endplates 204 and 206 away from one another, thereby increasing the axial height of vertebral insert 200. The first endplate 204 can include a pair of openings 212 and 214 through which bone graft material can be received or deposited. Likewise, the second endplate 206 can have one or more similar openings. In addition to these features, the vertebral insert 200 may include an interference nut 216 that is operably attached to a rear section (e.g., a trailing end) of the body portion 202, as well as a pair of stabilization members 218, 220. In some examples, endplates 204 and 206 may be formed of PEEK or another suitable material.

FIG. 10 illustrates an exploded view of a vertebral insert 200, while FIG. 11 shows a top view of the same device with a first endplate 204 removed. As shown in both views, a translation member 208 may include at least three expansion portions 222, 224, and 226, which may be connected via bridge portions 227. The expansion portions 222, 224, and 226 each may have angled surfaces that are configured to engage grooved portions of the first and second endplates 204 and 206. In some examples, the angled surfaces may be of similar angles, while in other examples, the angled surfaces may be of different angles. In at least some examples, providing at least three expansion portions 222, 224 and 226 may allow for an even expansion along a majority of the length of the body portion 202 of the vertebral insert 200.

The translation member 208 may be received in the central opening of the body portion 202. The body portion 202 may include a first end 228 and a second end 230. In some examples, the first end 228 may include one or more apertures 232, 234 as shown in FIGS. 10 and 11. These apertures 232, 234 may receive one or more stabilization members 218, 220.

In some examples, the stabilization members 218, 220 each may include a first substantially smooth portion 236, 238, respectively, and a second threaded portion 240, 242, respectively. The stabilization members 218, 220 may be inserted through the apertures 232, 234 of the body portion 202, with the threaded portions 240, 242 serving as the leading end that enters the apertures. After passing through the apertures 232, 234 of the body portion 202, the stabilization members 218, 220 may come into contact with a side of the translation member 208. In some examples, the threaded portions 240, 242 of the stabilization members 218, 220 may be threaded into mateable threaded surfaces of the translation member 208. In some examples, by using a pair of stabilization members 218, 220 as shown in FIGS. 10 and 11 on a first end of the body portion 202, rocking of the body portion 202 during expansion and contraction of the device 10 may be prevented.

While the illustrated example in FIGS. 10 and 11 show a pair of stabilization members 218, 220, in other examples, a single stabilization member or more than two stabilization members can be used to assist in preventing rocking of the body portion 202. In addition, while the stabilization members 218, 220 are illustrated as having a substantially cylindrical surface section, in other examples, the stabilization members 218, 220 can include other shapes and geometries. For example, in other examples, the stabilization members 218, 220 can have a surface that includes at least one edge or corner.

As shown in FIGS. 10 and 11, the body portion 202 also may include interference nut 216 that is positioned within a rear section of the body portion 202. In some examples, the interference nut 216 may be separate and removable from the body portion 202, while in other examples, the interference nut 216 may not be removable from the body portion 202. In some examples, the interference nut 216 may include a square nut that is operably connected to a rear section of the body portion 202. The interference nut 216 can be mateably connected to a rear of the body portion 202, for example, via a dove-tail type cut that encapsulates the interference nut 216. The interference nut 216 can be advantageously formed of a biocompatible material. In some examples, the interference nut 216 may be formed of PEEK.

The interference nut 216 can include a hole (not shown) that is capable of receiving the actuation member 210 therethrough. The actuation member 210, which can comprise a threaded set screw, may pass through the interference nut 216 and into contact with the translation member 208, as best shown in FIG. 11. The interference nut 216 may serve to add drag to the actuation member 210 as it passes therethrough, thereby establishing an interference fit. By providing an interference fit, the risk of the actuation member 210 being loosened prior to or during use may be minimized.

A vertebral insert 300 is shown in FIG. 12 that may be substantially similar to vertebral insert 200 except that a body portion 302 may be utilized instead of body portion 202. Vertebral insert 300 may include first and second endplates 304 and 306 that may include one or more features of first and second endplates 204 and 206 of vertebral insert 200. Body portion 302 may be substantially similar to body portion 202 except that an elongate member 308 may extend from a longitudinal side surface 310 of body portion 302. Elongate member 308 may generally have a T-shaped cross section that extends along a portion of longitudinal side surface 310, although other suitable configurations are also contemplated. A stabilization aperture 312 may be disposed at a middle portion of elongate member 308. Stabilization aperture 312 may be configured to receive a threaded portion of a stabilization member (not shown) to couple body portion 302 to a translation member (not shown, but similar to translation member 208 described with reference to FIG. 11). Thus, stabilization aperture 312, in at least some examples, may help to provide rotational stability to the translation member relative to the body portion 302 prior to or during use of the vertebral insert 300.

Once vertebral insert 300 is installed between vertebral bodies as shown in FIGS. 13 and 14, the superior-inferior height (e.g., the distance between endplates 304 and 306) may be increased. When vertebral insert 300 is moved to the expanded height, a lateral spacer 340 also may be inserted between vertebral bodies 2 and 4. In other examples, lateral spacer 340 may be inserted into the intervertebral space and coupled to vertebral insert 300 before the height of vertebral insert 300 is increased. Lateral spacer 340 may be configured to mate with vertebral insert 300. Lateral spacer 340 may extend from a first, trailing end 342 toward a second, leading end 344. Lateral spacer 340 may include a groove or channel 346 configured to mate with elongate member 308 of body portion 302. Channel 346 may be at least partially defined by one or more rails 348. The ends of channel 346 and rails 348 may terminate at a gap 369 which extends in the superior-inferior directions. Gap 369 may facilitate machining of lateral spacer 340 and may increase the amount of graft that can be applied to vertebral insert 300. In some examples, any additional number of gaps 369 may be included along the length of channel 346 and rails 348. That is, channel 346 and rails 348 may include a series of interrupted channels and rails that through which elongate member 308 of body portion 302 may pass through. In some examples, elongate member 308, channel 346, and rails 348 may form a tongue and groove joint, although other suitable connections are also contemplated. Gap 369 may be configured to separate channel 346 and rails 348 from a stop surface 364 that is configured to abut elongate member 308 of vertebral insert 300. In some examples, lateral spacer 340 may define a cavity 350 that may be similar to cavities 150 and 167 described above. Cavity 350 may be packed with bone graft or bone-growth inducing substances in a substantially similar manner as cavities 150 and 167. In some examples, cavity 350 may be at least partially defined by an arc portion 352 that may approximate the anterior curvature of a vertebral body. However, any or all portions of vertebral insert 300 can be formed in any other suitable configuration depending upon the geometry of the vertebral bodies between which it is to be inserted.

Figure 16:
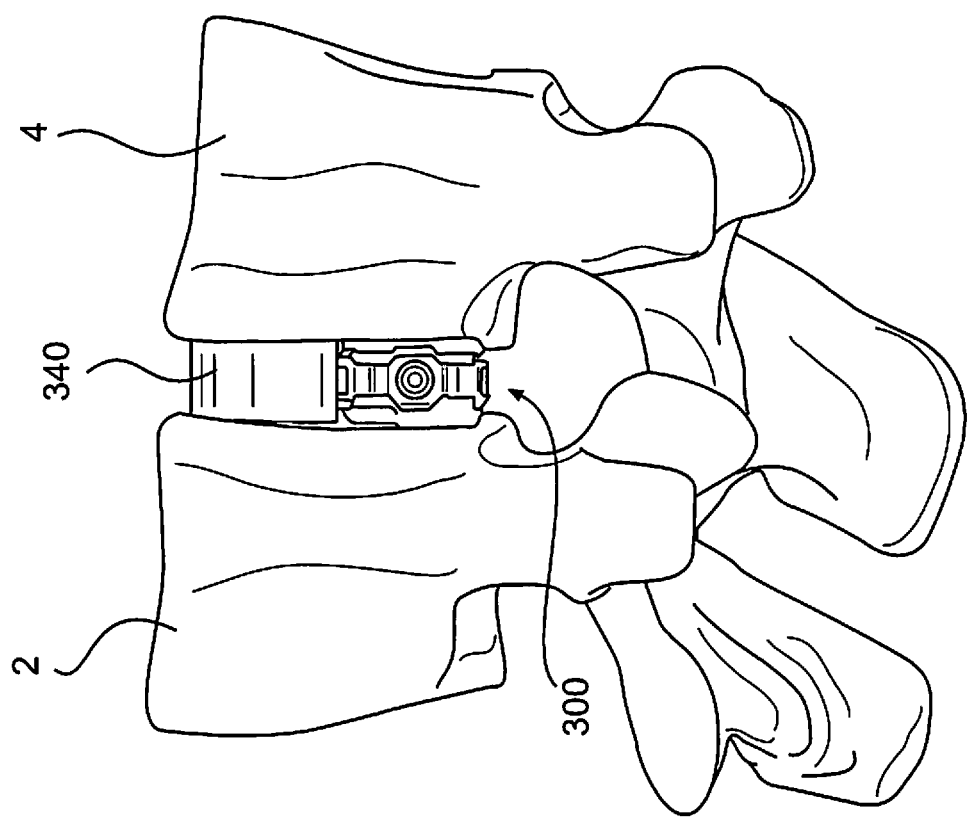
Figure 15:
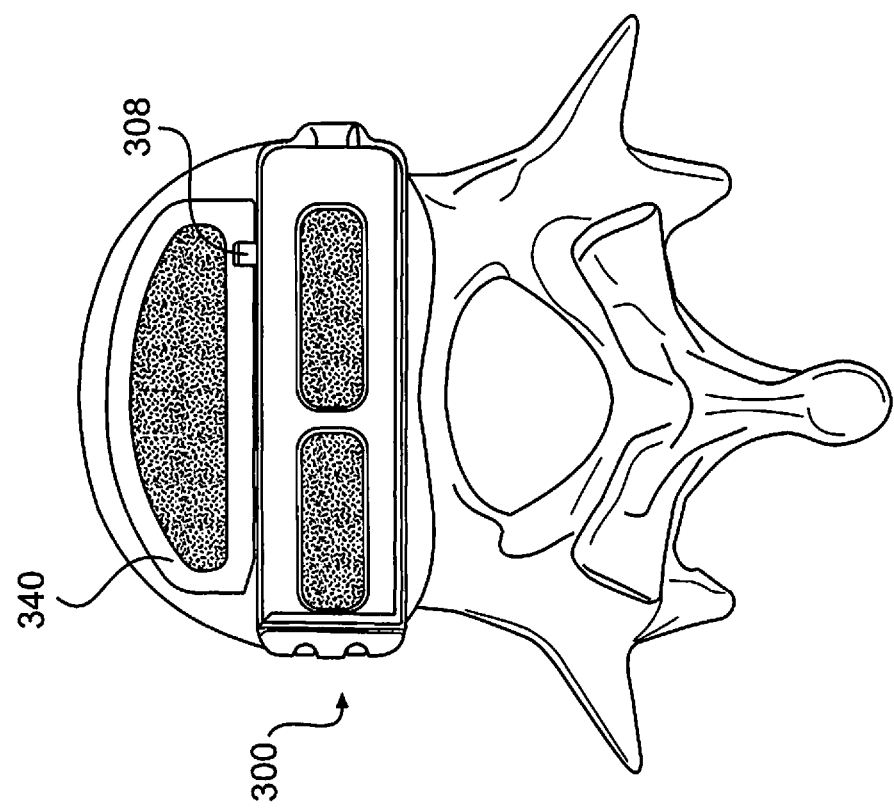

In one example, body portion 302 may be positioned at the posterior end between two vertebral bodies. However, it is also contemplated that body portion 302 also may be positioned toward the anterior end. Then, lateral spacer 340 may be inserted at the anterior end (if body portion 302 is positioned at the posterior end) or the posterior end (if body portion 302 is positioned at the anterior end). It is also contemplated that body portion 302 may include an additional elongate member 308 at a longitudinal side surface opposite of longitudinal side surface 310 to allow body portion 302 to mate with two different lateral spacers. For example, in some examples, body portion 302 may accommodate an additional lateral spacer, e.g., as shown in FIGS. 1-9. FIG. 15 shows a top view of vertebral insert 300 and lateral spacer 340 installed on a vertebral body. FIG. 16 is a side view of vertebral insert 300 and lateral spacer 340 installed between vertebral bodies. In some examples, one or more of vertebral insert 300 and lateral spacer 340 may be configured to provide lordosis correction. In some examples, vertebral insert 300 and lateral spacer 340 together may form a continuous angled and ramped surface. In other examples, vertebral insert 300 and lateral spacer 340 each may be ramped at different angles to provide differing degrees of lordosis correction based on the specific geometries of vertebral bodies between which they are inserted.

In some examples, vertebral insert 300 and lateral spacer 340 may be secured between vertebral bodies 2 and 4 via a minimally invasive plate system that is configured to provide stabilization through a lateral approach. The plate system may include brackets, bone screws, blocking screws, and other suitable elements to maintain vertebral insert 300 and lateral spacer 340 between vertebral bodies 2 and 4.

In some examples, vertebral insert 300 and lateral spacer 340 may be delivered by a minimally invasive (MIS) lateral lumbar interbody fusion (LLIF) approach. Vertebral insert 300 and lateral spacer 340 may be configured to provide increased surface area over conventional vertebral inserts. Vertebral insert 300 may provide improved spacer fit by allowing for anterior and/or posterior spacer selection. In some examples, vertebral insert 300 and lateral spacer 340 may provide increased total surface area contact with vertebral bodies while also engaging harder bone around the apophyseal ring. In still further examples, vertebral insert 300 and lateral spacer 340 may provide for increased amount of bone graft or bone-growth inducing substances to be utilized over conventional devices. In some examples, vertebral insert 300 may provide for more even weight load distribution, reduce cage subsidence, provide a large fusion bed graft area, and/or a higher degree of height and lordotic correction by having separate posterior and/or anterior spacers.

Another example of a vertebral insert 400 is shown in FIGS. 17-20. Vertebral insert 400 may be reciprocally movable between a first, collapsed configuration (shown in FIG. 17) and a second, expanded configuration (shown in FIG. 18). In some examples, vertebral insert 400 may be a collapsible and expandable ring-shaped member that defines a cavity 460. Cavity 460 may be packed with bone graft in a substantially similar manner as set forth above. Vertebral insert 400 may extend from a first, trailing end 402 toward a second, leading end 404. Vertebral insert 400 may include a first linkage 406, a second linkage 408, a third linkage 410, and a fourth linkage 412.

First linkage 406 may include a hollow elongate portion 414 and a flange portion 416. Hollow elongate portion 414 may be generally cylindrical or have another suitable shape. Flange portion 416 may extend radially outward from hollow elongate portion 414 at a middle longitudinal section or other suitable longitudinal section. An elongate member 418 (e.g., a rod) may extend from flange portion 416 to couple first linkage 406 with second linkage 408. Elongate member 418 also may prevent the rotation of first linkage 406 relative to second linkage 408. In an alternative example, hollow elongate portion 414 may be formed in a shape configured to prevent the relative rotation of the first and second linkages 406 and 408 (such as, e.g., square, rectangular, star, or the like). Flange portion 416 also may include features 417 to couple first linkage 406 to third linkage 410. Features 417 may include a pair of flanges configured to form a joint with an extension of third linkage 410 (e.g., a bridle joint, a mortise and tenon joint, or another suitable joint or connection). In some examples, the pair of flanges may have apertures or pin holes that are aligned with one another to receive a securing mechanism such as, e.g., a pin that extends through each of the pair of flanges and the extension of third linkage 410, so as to rotatably couple first linkage 406 with third linkage 410.

Second linkage 408 may include an end portion 420 having a recess 422 (referring to FIG. 18) disposed therethrough that is configured to slidably receive hollow elongate portion 414 of first linkage 406. A longitudinal portion 424 may extend from end portion 420 toward a distraction end 426. End portion 420 may be disposed at an angle (e.g., 90 degrees) relative to longitudinal portion 424. A recess 427 (shown in dotted lines in FIG. 17) may extend through end portion 420 and at least partially through longitudinal portion 424 to receive elongate member 418 therein. Distraction end 426 may be disposed at second, leading end 404 of vertebral insert 400 and may be wedged, bladed, or have another suitable shape to facilitate the distraction of a pair of vertebral bodies upon insertion of vertebral insert 400. That is to say, distraction end 426 may include a tapered configuration. In some examples, because of the relationship of recess 422 and elongate portion 414, and of elongate member 418 and recess 427, first linkage 406 and second linkage 408 may be configured to slidably and longitudinally move with respect to one another.

Third linkage 410 may be a generally elbow shaped member that may be coupled to first linkage 406 (via features 417 described above) at one end, and coupled to fourth linkage 412 at a second end. Third linkage 410 may be formed from two arms 428 that converge at a bend 430 joining the two arms 428. In some examples, the two arms 428 may form an oblique angle with respect to one another. The second end of third linkage 410 may include mating features 432 that may be substantially similar to mating features 417 of first linkage 406. The mating features 432 may be configured to receive an extension of fourth linkage 412 to form a joint such as, e.g., a bridle type joint, a mortise and tenon type joint, or another suitable joint or connection.

Fourth linkage 412 also may be a generally elbow shaped member that is coupled to third linkage 410 at one end, and coupled to second linkage 408 at another end. Each end of fourth linkage 412 may include any suitable connector, extension, flange, coupling, or the like to mate with a corresponding feature on third linkage 410 and/or second linkage 408. Third and fourth linkages 410 and 412 together, when vertebral insert 400 is in the expanded configuration, may form an arc portion that generally approximates the anterior curvature of a vertebral body. In the collapsed configuration of vertebral insert 400, third and fourth linkages 410 and 412 may be buckled laterally inward. In the expanded configuration of vertebral insert 400, third and fourth linkages 410 and 412 may bow laterally outward. In some examples, the superior-inferior height of vertebral insert 400 may remain unchanged in both the collapsed and expanded configuration of vertebral insert 400.

Figure 17:
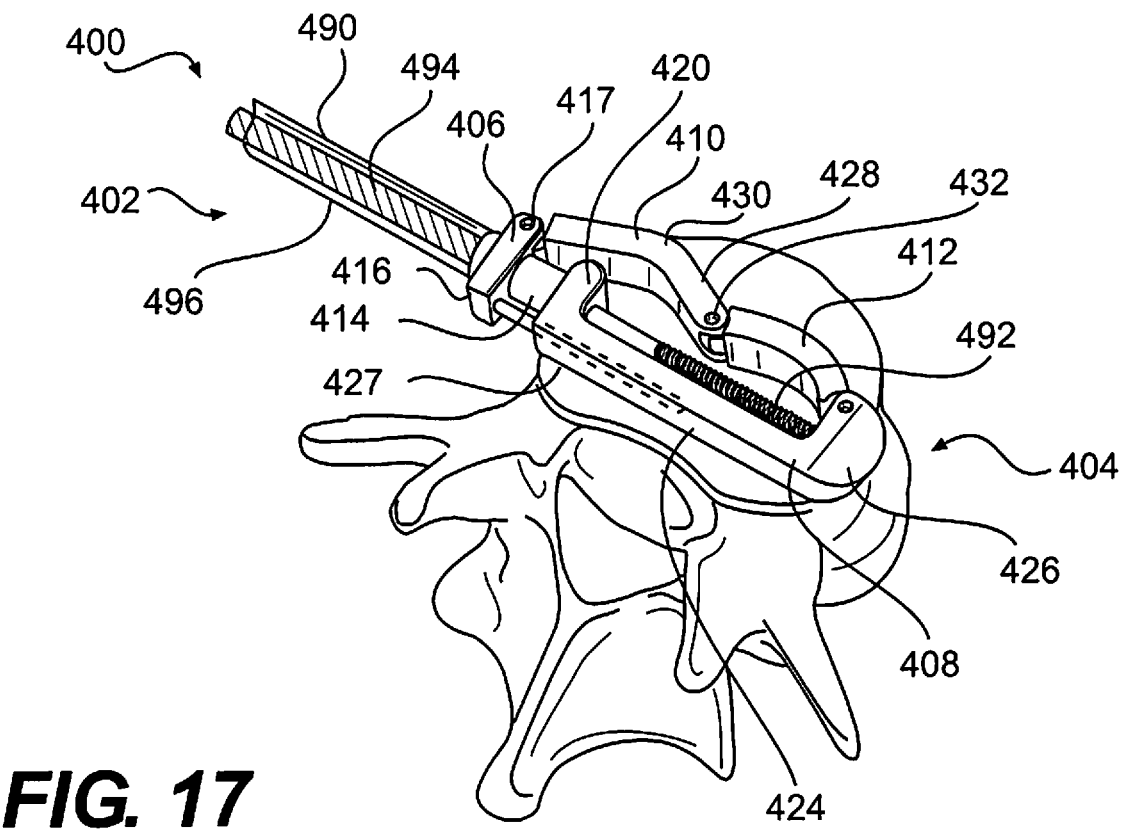
FIGS. 17-20 depict a vertebral insert in accordance with an example of the present disclosure.

The various linkages described with reference to FIG. 17 may be formed of any suitable biocompatible material, such as, e.g., titanium, PEEK, or the like. In some examples, the linkages may be treated with a titanium and/or hydroxyapatite plasma spray coating to encourage bony on-growth, improving the strength and stability of the connection between the respective component and the underlying bone (e.g., a vertebral body).

Figure 18:
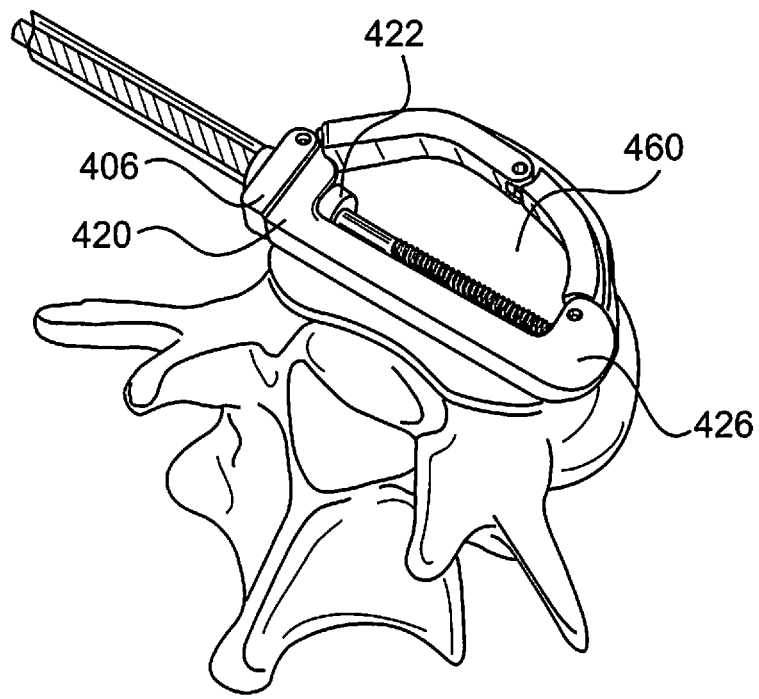
Figure 19:
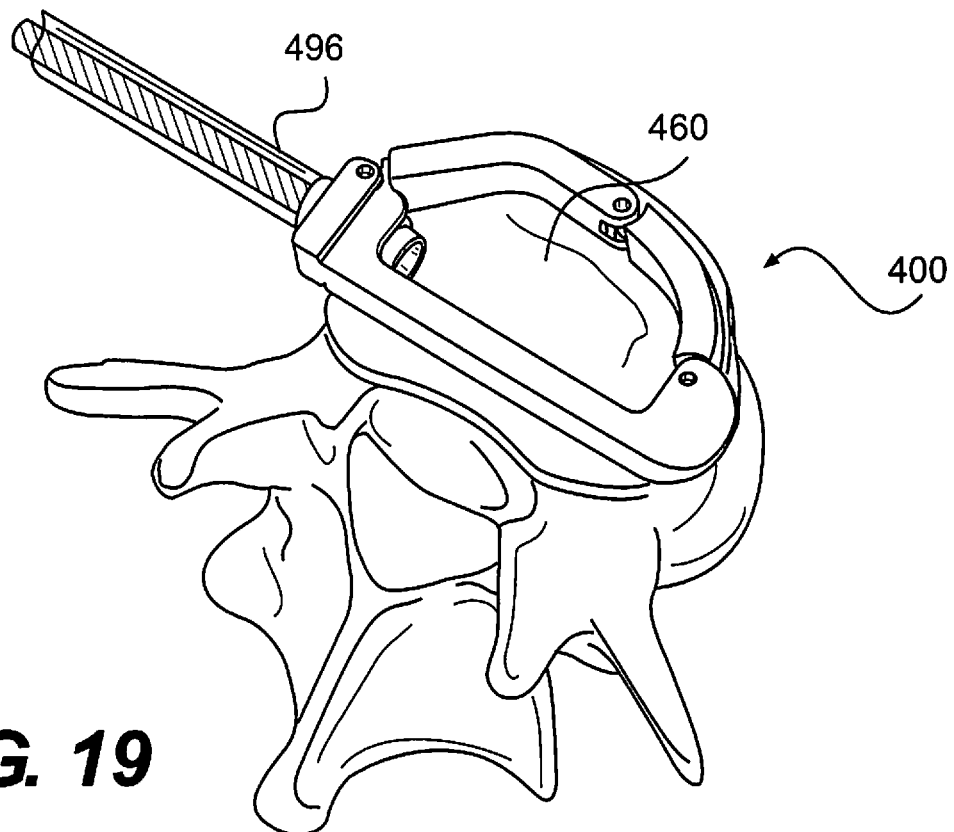
Figure 20:
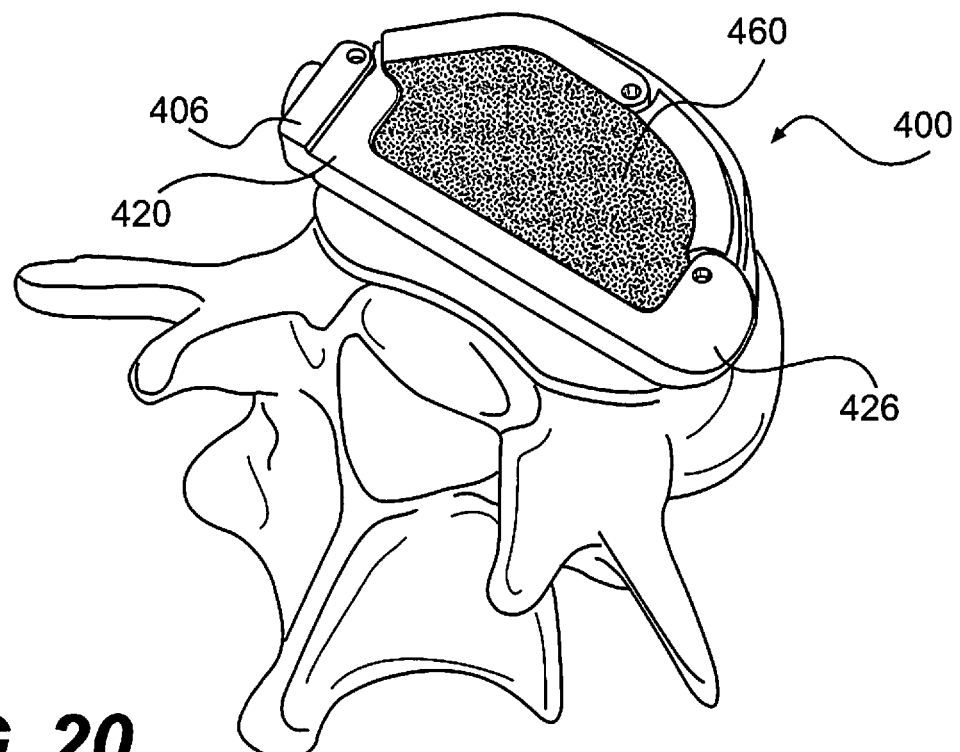
Figure 21:
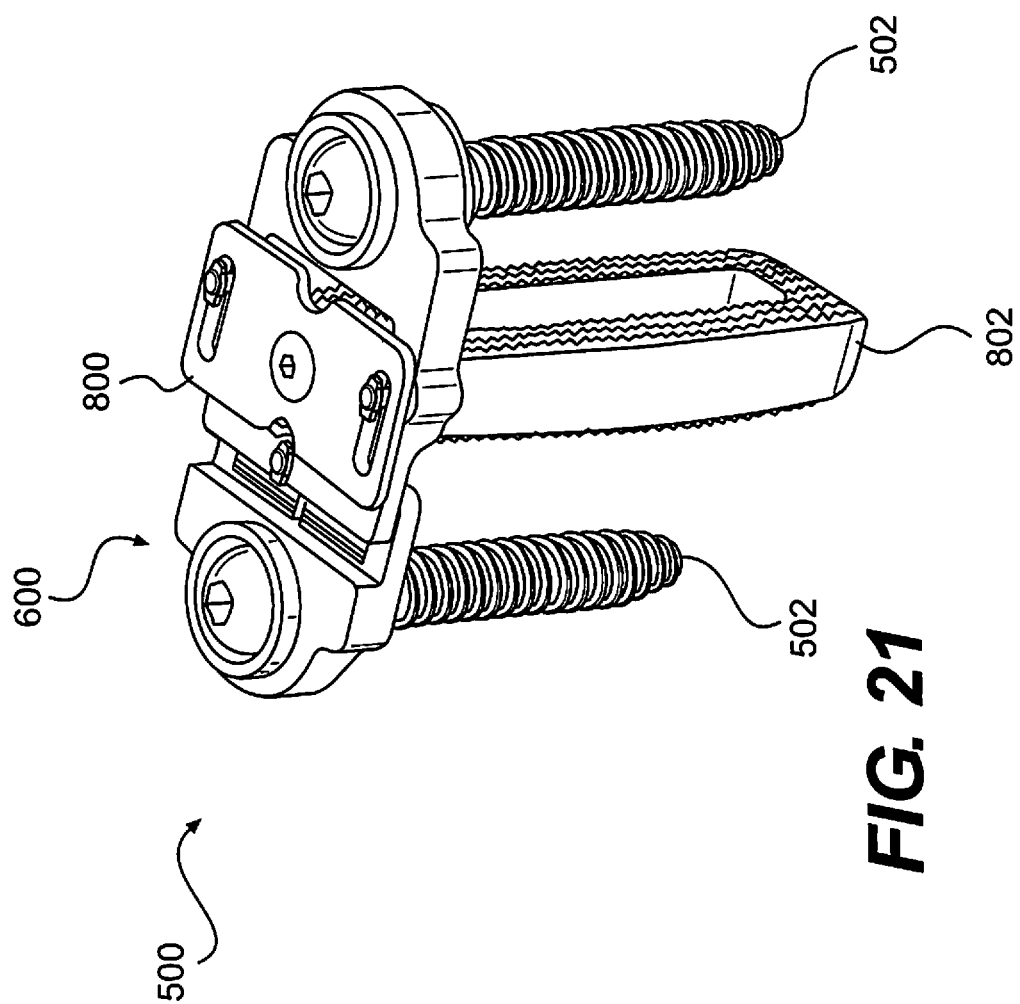
FIG. 21 is a perspective view of a spacer assembly in accordance with an example of the present disclosure.

Vertebral insert 400 may be inserted between vertebral bodies while in a collapsed configuration (shown in FIG. 17) while attached to a positioning tool 490, to another suitable tool, or unattached to a tool. A holding member 492 may be disposed at a distal end of positioning tool 490 and may extend through hollow elongate portion 414 and end portion 420 to couple to a recess or bore (not shown) disposed within distraction end 426 of second linkage 408. In one example, holding member 492 may be a threaded screw extending from a proximal portion 484. Holding member 492 may be fastened to distraction end 426 in some examples. An elongate drive member 496 may be slidable relative to holding member 492. In some embodiments, elongate drive member 496 may be hollow. Once holding member 492 is fastened to distraction end 426 of second linkage 408, driving member 496 then may be coupled to a first end of first linkage 406 as shown in FIG. 17 (via, e.g., threads or the like). Drive member 496 may be advanced distally to push first linkage 406 from first end 402 toward second end 404 of vertebral insert 400, causing vertebral insert 400 to move from the first, collapsed configuration to the second, expanded configuration (FIG. 18). Once vertebral insert 400 is in the expanded configuration, a suitable locking mechanism such as, e.g., a tang, blocking screw, latch, or other suitable locking mechanism may stabilize vertebral insert 400 into the expanded configuration. Once locked into the expanded configuration, holding member 492 and drive member 496 may be disconnected and withdrawn from the patient. In some examples, a distal portion of holding member 492 may be left within vertebral insert 400 and only proximal portion 494 and drive member 496 may be withdrawn. Thus, in some examples, holding member 492 may be configured to lock vertebral insert into the expanded configuration, via, e.g., a rotatable locking flange (not shown) disposed at a proximal end of holding member 492. Subsequently, bone graft may be packed into cavity 460 via, e.g., a lumen of elongate drive member 496.

A spacer assembly 500 is shown in FIGS. 21-36. Spacer assembly 500 may include a plate assembly 600, one or more fastening members 502, a bracket 800, and a spacer 802. As best seen in FIGS. 22 and 23, plate assembly 600 may extend from a first end 602 toward a second 604. In some embodiments, plate assembly 600 may include a plurality of plates moveable relative to each other, as described below. For example, a first plate 606 may extend from first end 602 toward second end 604, while a second plate 608 may extend from second end 604 toward first end 602. In embodiments having a single plate (not shown), however, a cavity extending through plate assembly 600 may be selectively adjustable.

With specific reference to FIGS. 22-24, first plate 606 may include a substantially rectangular portion 610 and a substantially semi-circular portion 612 extending from rectangular portion 610. As shown in FIG. 22, first plate 606 may further include a throughbore 614. Throughbore 614 may be disposed completely in semi-circular portion 612, completely in rectangular portion 610, or partially in semi-circular portion 612 and partially in rectangular portion 610, as shown. On a first side 616 of first plate 606, throughbore 614 may include an opening 618. Opening 618 may be surrounded by a raised lip 620 extending around the periphery of opening 618. Raised lip 620 may include any suitable configuration. In one embodiment, raised lip 620 may include a substantially square cross-sectional configuration. Those of ordinary skill in the art, however, will recognize that raised lip 620 may include any suitable cross-sectional configuration. Though the depicted embodiment shows raised lip 620 as continuously extending around opening 618, raised lip 620 may include one or more breaks, such that it does not extend continuously around opening 618. In some embodiments, opening 618 may further include a radially inward lip 622 extending away from a wall defining opening 618.

With continued reference to FIG. 22, first side 616 may further include a stepped portion 624. Stepped portion 624 may be spaced from a surface 626 by a vertical wall 628 (shown in FIG. 24). Stepped portion 624 may include any suitable configuration. In one embodiment, stepped portion 624 may include a substantially constant cross-sectional dimension. However, in some embodiments, stepped portion 624 may include a tapered cross-sectional configuration. Stepped portion 624 may have a smaller cross-sectional dimension (e.g., thickness) relative to a remainder of first plate 606. Stepped portion 624 may include a surface on first side 616 having one or more geometric configurations 630 to increase friction. For example, geometric configurations 630 may include one or more teeth, ridges, divots, cavities, or other similar structures. Further, stepped portion 624 may define an elongated channel 632 extending through stepped portion 624. Although a single elongate channel 632 is depicted, stepped portion 624 may include a plurality of channels or cavities. Elongate channel 632 may include any suitable configuration. As will be described in further detail below, elongate channel 632 may be configured to receive a portion of a locking member 634.

With reference now to FIG. 23, first plate 606 may include a second side 636 disposed opposite to the first side 616. Second side 636 may be substantially planar. In some embodiments, an opening 638 of throughbore 614 may be surrounded by a raised atraumatic lip 640. Lip 640 may include any suitable configuration, including, but not limited to, a curved outer periphery. A portion of lip 640 may include a cutout 642 corresponding to an end of elongate channel 632. As can also be seen in FIG. 23, elongate channel 632 may extend through first plate 606 to an opening 644 on second side 636. Opening 644 may include counterbore features extending around a periphery of opening 644 to receive an end of a locking member 634.

With continued reference to FIGS. 22-24, second plate 608 may include a substantially rectangular portion 650 and a substantially semi-circular portion 652 extending from rectangular portion 650. Second plate 608 may further include a throughbore 654. Throughbore 654 may be disposed completely in semi-circular portion 652, completely in rectangular portion 650, or partially in semi-circular portion 2215 and partially in rectangular portion 650, as shown. On a first side 656 of second plate 608, throughbore 654 may include an opening 658. Opening 658 may be surrounded by a raised lip 660 extending around the periphery of opening 658. Raised lip 660 may include any of the features described above with respect to raised lip 620. In some embodiments, opening 658 may further include a radially inward lip 662 extending away from a wall defining opening 658.

Figure 27:
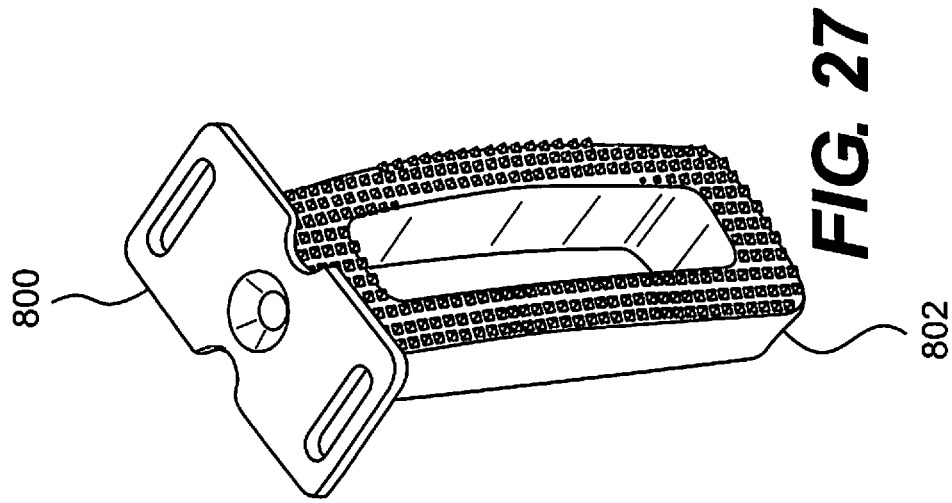
FIGS. 25-27 are perspective views of a bracket and spacer in accordance with an example of the present disclosure.
Figure 26:
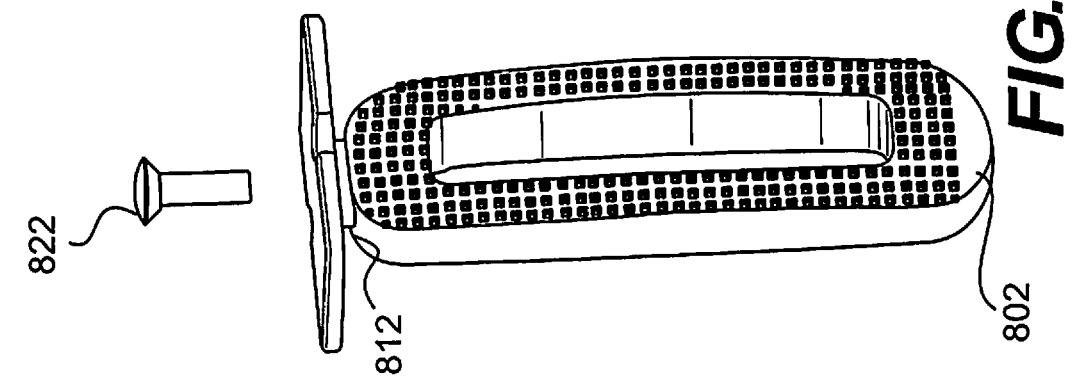
Figure 25:
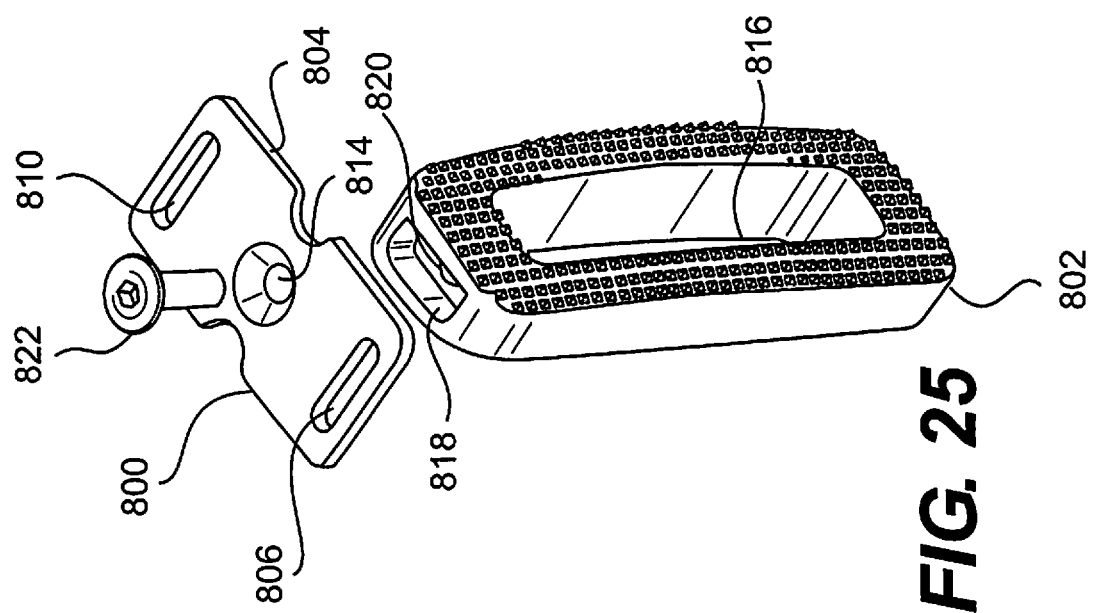

In the embodiment shown in FIGS. 22-24, rectangular portion 650 may define a cavity 664 (e.g., a rectangular cavity configured to receive a vertebral spacer 802 shown in FIGS. 25-27). Locking member 634 may extend through a recess disposed in an end wall 666 that at least partially defines cavity 664. The end wall 636 may include a protrusion 668 that extends into cavity 664. The protrusion 668 may accommodate various features (e.g., locking features) associated with locking member 634. In some examples, locking member 634 may include a head portion 670 that abuts the first side 656 of second plate 608. Cavity 664 also may be at least partially defined by a side wall 672 and side wall 674. In some examples, side walls 672 and 674 may be substantially parallel to one another and orthogonal to end wall 636. A locking member 676 may extend through a recess disposed in side wall 672 while a locking member 678 may extend through a recess disposed in side wall 674. Locking members 676 and 678 may include one or more locking features described with reference to locking member 634. Side wall 672 may include a protrusion 680 and side wall 674 may include a protrusion 682. Protrusions 680 and 682 may accommodate locking features of locking members 676 and 678, respectively, and may be configured to extend away from cavity 664 in opposite directions.

With reference now to FIG. 23, second plate 608 may include a second side 686 disposed opposite to the first side 656. Second side 686 may be substantially planar. In some embodiments, an opening 688 of throughbore 654 may be surrounded by a raised atraumatic lip 690. Lip 690 may include may include one or more features described above with reference to lip 640. Second side 686 may further include a stepped portion 694 disposed on end wall 674. Stepped portion 694 may be spaced from a surface 696 by a vertical wall 698 (shown in FIG. 23). Stepped portion 694 may include any suitable configuration including those described with reference to stepped portion 624 of first plate 606, and may include geometric features 700 that may be substantially similar to geometric features 630. Second side 686 also may include a stepped portion 704 that is disposed along end wall 672. Stepped portion 704 may be spaced from surface 696 by a vertical wall 708 and may include geometric features 710 that are substantially similar to geometric features 630 and 700. The stepped portions of second plate 608 (e.g., stepped portions 694, 704 and a stepped portion of end wall 666) may have a smaller cross-sectional dimension (e.g., thickness) than a remainder of second plate 608. Side walls 672 and 674 also may include counterbore features 712 and 714 that may be configured to receive portions of locking members 676 and 678, respectively.

As described above, first and second plates 606 and 608 may be movable relative to one another when coupled via locking member 634. In some examples, stepped portion 624 of first plate 606 may be slidably coupled to stepped portions 694 and 704 of second plate 608. When coupled to one another, first and second plates 606 and 608 may form an adjustable joint or other suitable connection. In one example, first and second plates 606 and 608 may form a half lap splice joint, although other suitable connections are also contemplated.

The relative movement of first plate 606 and 608 with respect to one another may define an effective opening of cavity 664. That is, cavity 664 may be movable between a first, fully-open configuration (shown in FIG. 24), and a second, partially-open configuration (shown in FIG. 22). In the second, partially-open configuration, stepped portion 624 of first plate 606 may extend over and cover cavity 664, reducing the effective opening size of cavity 664. That is, stepped portion 624 may extend over cavity 664 to reduce the size of a vertebral spacer that can be received by cavity 664. It is also contemplated that cavity 664 may include any number of intermediate configurations between the first, fully-open configuration and the second, partially-open configuration.

Locking member 634 may be reciprocally movable between a plurality of configurations and may be configured to couple first and second plates 606 and 608 to one another. In a first configuration, locking member 634 may couple first plate 606 to second plate 608 and may permit the relative movement of first and second plates 606 and 608 with respect to one another. In a second configuration, locking member 634 may fix the orientation of first plate 606 with respect to second plate 608 by any suitable mechanism such as, e.g., tightening a threaded engagement, moving a locking flange or other mechanism into a locking position, or the like.

FIGS. 25-27 depict exploded and assembled views of a bracket 800 and a spacer 802. Bracket 800 may be a bracket configured to couple to both spacer 802 and plate assembly 600 described above. Bracket 800 may include a generally rectangular elongate surface 804 having a first elongate cavity 806 and a second elongate cavity 810 extending through elongate surface 804. The lengths of elongate cavities 806 and 810 may be generally parallel to one another, and each may be generally perpendicular to the length of elongate surface 804, although other suitable configurations are also contemplated. Bracket 800 also may include a protrusion 812 (shown only in FIG. 26) that extends away from elongate surface 804. A bore 814 may extend through elongate surface 804 and protrusion 812 to receive a fastener (e.g., a threaded screw or the like). In some examples, bracket 800 may be curved at its lateral edges.

Spacer 802 may be any suitable intervertebral spacer. In the example shown in FIGS. 25-27, spacer 802 may be a generally rectangular spacer defining a cavity 816. Cavity 816 may be packed with bone graft or bone-growth inducing materials. A lateral end surface of spacer 802 may define a recess 818 and a bore 820 configured to receive protrusion 812 and fastener 822 respectively. Recess 818 and bore 820 of spacer 802 may be complimentary to protrusion 812 and fastener 822 so as to limit movement of bracket 800 and spacer 802 with respect to one another. Spacer 802 may be any suitable intervertebral spacer, and may include one or more of inferior surfaces, superior surfaces, biconvex surfaces, among others. In some examples, the surfaces of spacer 802 or any other bone contacting surface described in the present disclosure may include one or more of teeth, ridges, friction increasing elements, keels, or gripping or purchasing projections.

Figure 28:
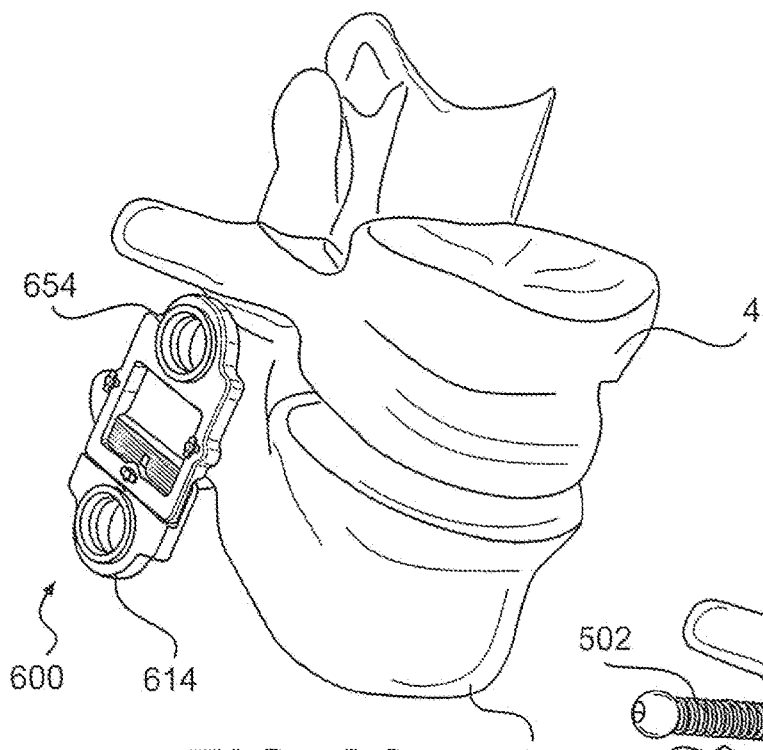
FIGS. 28-36 depict an exemplary method of installing a spacer assembly in accordance with an example of the present disclosure.
Figure 30:
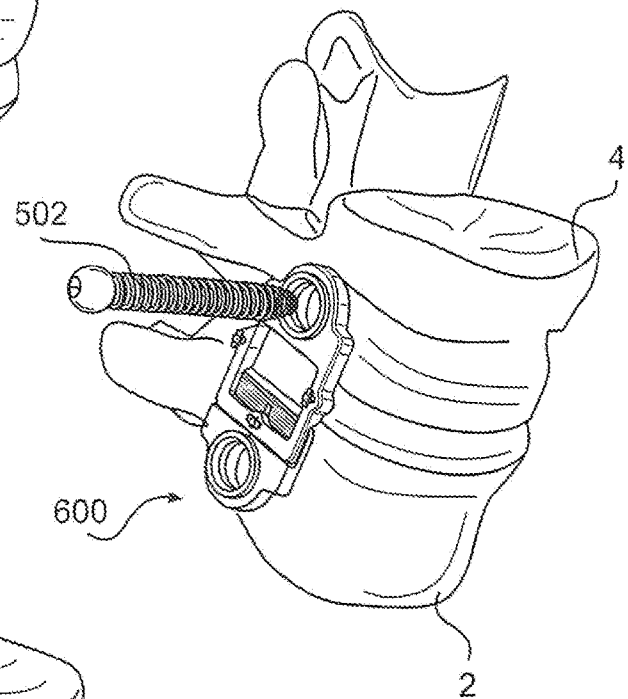
Figure 29:
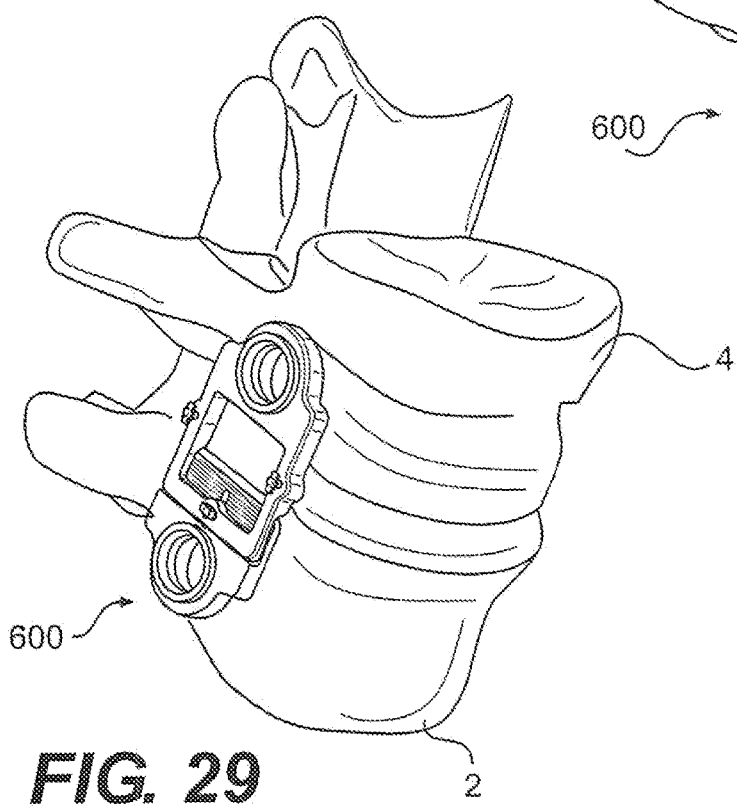
Figure 32:
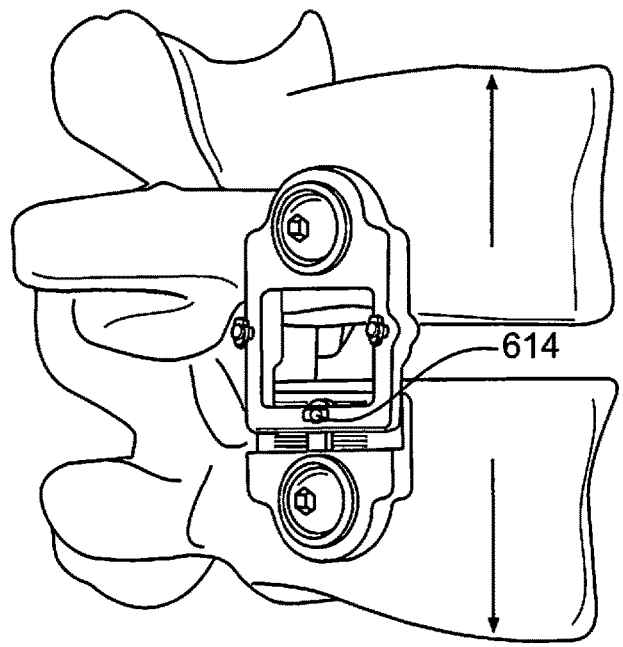
Figure 33:
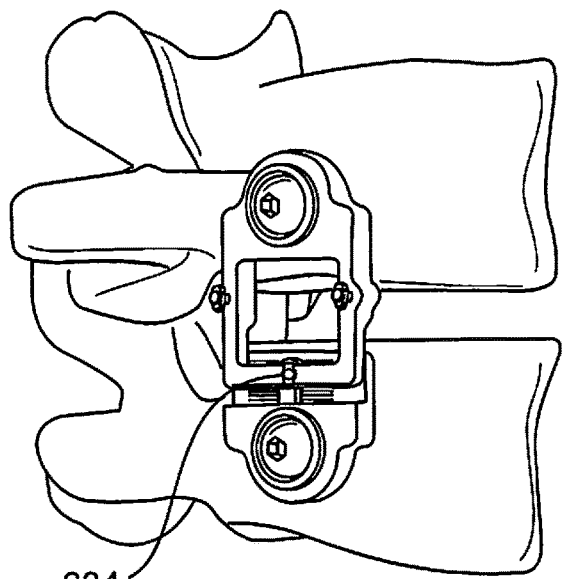
Figure 31:
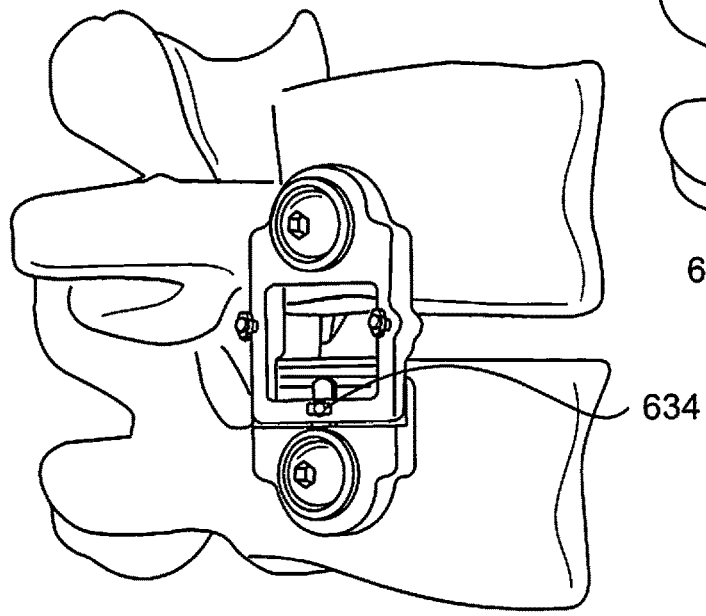

FIGS. 28-36 depict an exemplary method of installing spacer assembly 500 within a patient. Initially, plate assembly 600 may be brought in proximity with two vertebral bodies 2 and 4 (FIG. 28). In one example, during initial installation, first and second plates 606 and 608 may be in the second, partially-open configuration where cavity 628 has its smallest effective opening. As shown in FIG. 29, bore 654 may be aligned with vertebral body 4 while, bore 614 may be aligned with vertebral body 2. First and second plates 606 and 608 may be moved toward the fully-opened configuration depending upon the desired distance between vertebral bodies 2 and 4 to optimize fit. It is contemplated that in some examples, plate assembly 600 may be in an intermediate configuration between the first and second configurations at this stage such that cavity 664 is at an intermediate opening size. A fastening member 502 may then be used to secure one of first or second plates 606 and 608 to a respective vertebral body (FIG. 30), and another fastening member 502 may be used to secure another fastener 502 to secure the other of first and second plates 606 and 608 to a respective vertebral body (FIG. 31).

Once first and second plates 606 and 608 are secured to vertebral bodies 2 and 4, an operator may distract vertebral bodies 2 and 4 from one another via first and second plates 606 and 608. That is, an operator may move first and second plates 606 and 608 away from one another to move vertebral bodies 2 and 4 away from one another. Once vertebral bodies 2 and 4 have been moved away from one another (e.g., distracted) by a sufficient distance, an operator may lock the distracted position by moving locking member 634 from an unlocked configuration to a locked configuration, thereby locking the positions of first and second plates 606 and 608 and also vertebral bodies 2 and 4. It is further contemplated that the positions of first and second plates 606 and 608 may be fixed with respect to one another by any other suitable mechanism.

Figure 35:
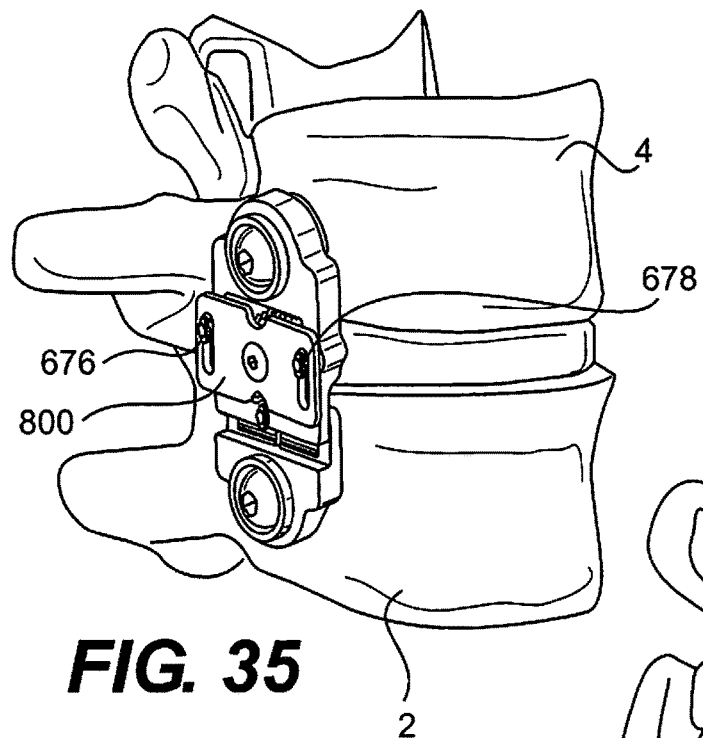
Figure 36:
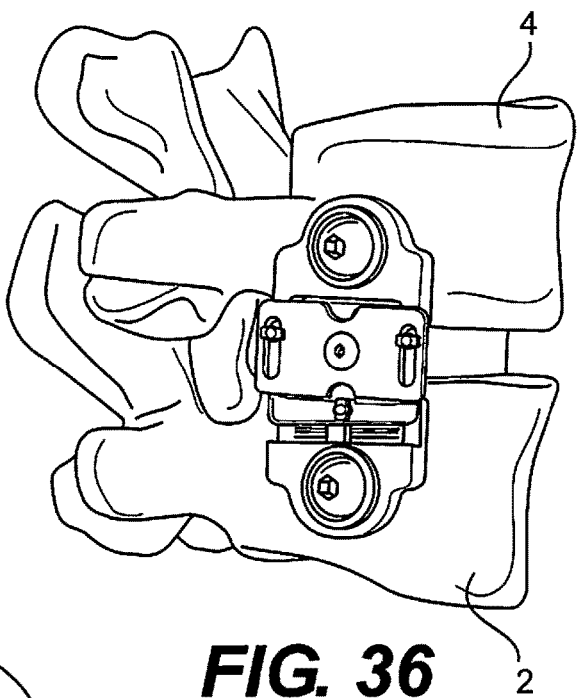
Figure 34:
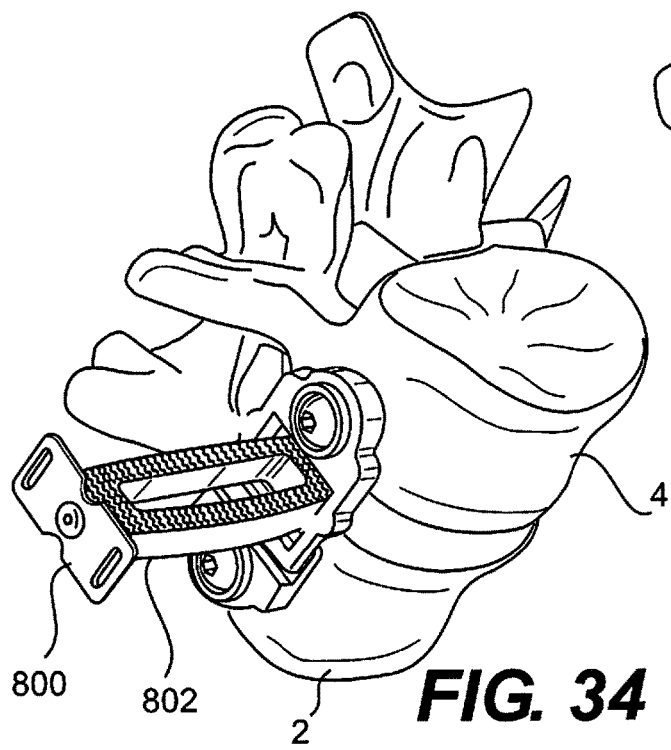

Once vertebral bodies 2 and 4 are distracted and locked into position, spacer 802 may be inserted through cavity 664 (FIGS. 34 and 35). As spacer 802 is moved between the vertebral bodies, bracket 800 may abut second plate 608 of plate assembly 600. Further, locking elements 676 and 678 may be positioned to extend through elongate cavities 806 and 810. The locking elements 676 and 678 may then be moved from an insertion configuration to a locking configuration, thereby securing spacer 802 between vertebral bodies 2 and 4.

Spacer assembly 500 may provide one or more of the following advantages, including: an increased tactile feel while distracting, an increased range of distraction height, increased bone graft size and placement, improved radiolucent viewing, decreased stress on endplates and reduced chance of subsidence, and the potential elimination of the need for posterior fixation.

Any aspect set forth in any example may be used with any other example set forth herein. Every device and apparatus set forth herein may be used in a suitable medical procedure, such as, e.g., a vertebral disc replacement procedure, and may be advanced through any suitable body lumen and body cavity.

It will be apparent to those skilled in the art that various modifications and variations can be made in the disclosed systems and processes without departing from the scope of the disclosure. Other examples of the disclosure will be apparent to those skilled in the art from consideration of the specification and practice of the embodiments disclosed herein. It is intended that the specification and examples be considered as exemplary only.

I claim:

1. A vertebral spacer assembly, comprising:
a vertically expandable spacer having first and second endplates and a body disposed between the two endplates;
a plurality of differently shaped spacer inserts each adapted to be slidably coupled to the expandable spacer in a lateral direction,
wherein the body of the vertically expandable spacer includes an elongate guide disposed on a side surface of the body,
wherein the vertically expandable spacer includes a translator coupled between the body and the two endplates and adapted to vertically move the first endplate relative to the second endplate, and
wherein the elongate guide includes a stabilization aperture for receiving a stabilizer to couple the body to the translator.

2. The vertebral spacer assembly of claim 1, wherein each spacer insert includes an insert guide disposed on a side surface of the spacer insert and adapted to slidably mate with the elongate guide of the body.

3. The vertebral spacer assembly of claim 2, wherein the elongate guide includes an elongate rib extending laterally and longitudinally from the side surface of the body.

4. The vertebral spacer assembly of claim 3, wherein the insert guide includes an elongate recess sized to be slidably mated with the elongate rib of the body.

5. The vertebral spacer assembly of claim 4, wherein each spacer insert includes a gap disposed at one end of the elongate recess and extending in a superior-inferior direction.

6. The vertebral spacer assembly of claim 3, wherein the elongate rib has a t-shaped cross section.

7. The vertebral spacer assembly of claim 1, wherein each spacer insert includes at least one cavity for receiving bone graft.

8. The vertebral spacer assembly of claim 1, wherein the vertically expandable spacer includes:
an actuator rotatably coupled to the body;
a translator coupled to the actuator and disposed between the two endplates, the actuator causing the translator to translate relative to the body which in turn causes the first endplate to move vertically relative to the second endplate.

9. A vertebral spacer assembly, comprising:
a vertically expandable spacer including:
first and second endplates;
a body disposed between the two endplates;
an actuator rotatably coupled to the body;
a translator coupled to the actuator and disposed between the two endplates, the actuator causing the translator to translate relative to the body which in turn causes the first endplate to move vertically relative to the second endplate;
a plurality of differently shaped spacer inserts each adapted to be slidably coupled to the expandable spacer in a lateral direction.

10. The vertebral spacer assembly of claim 9, wherein the body of the vertically expandable spacer includes an elongate guide disposed on a side surface of the body.

11. The vertebral spacer assembly of claim 10, wherein each spacer insert includes an insert guide disposed on a side surface of the spacer insert and adapted to slidably mate with the elongate guide of the body.

12. The vertebral spacer assembly of claim 11, wherein the elongate guide includes an elongate rib extending laterally and longitudinally from the side surface of the body.

13. The vertebral spacer assembly of claim 12, wherein the insert guide includes an elongate recess sized to be slidably mated with the elongate rib of the body.

14. The vertebral spacer assembly of claim 13, wherein the spacer insert includes a gap disposed at one end of the elongate recess and extending in a superior-inferior direction.

15. The vertebral spacer assembly of claim 12, wherein the elongate rib has a t-shaped cross section.

16. The vertebral spacer assembly of claim 10, wherein:
the vertically expandable spacer includes a translator coupled between the body and the two endplates and adapted to vertically move the first endplate relative to the second endplate; and
the elongate guide includes a stabilization aperture for receiving a stabilizer to couple the body to the translator.

17. The vertebral spacer assembly of claim 9, wherein the spacer insert includes at least one cavity for receiving bone graft.

18. The vertebral spacer assembly of claim 9, wherein:
the body of the vertically expandable spacer includes an elongate rib extending laterally and longitudinally from a side surface of the body;
the spacer insert includes an elongate recess sized to be slidably mated with the elongate rib of the body.

* * * * *